United States Patent [19]

Maestre

[11] Patent Number: 5,495,961

[45] Date of Patent: * Mar. 5, 1996

[54] PORTABLE PROGRAMMABLE MEDICATION ALARM DEVICE AND METHOD AND APPARATUS FOR PROGRAMMING AND USING THE SAME

[76] Inventor: Federico A. Maestre, 2 Hawthorne Pl.-Apt. 6M, Boston, Mass. 02114

[*] Notice: The portion of the term of this patent subsequent to Sep. 13, 2011, has been disclaimed.

[21] Appl. No.: 304,347

[22] Filed: Sep. 12, 1994

Related U.S. Application Data

[63] Continuation of Ser. No. 860,414, Mar. 30, 1992, Pat. No. 5,347,453.

[51] Int. Cl.$^6$ ................................................ G06F 159/00
[52] U.S. Cl. ................................................ 221/3; 368/10
[58] Field of Search ........................ 364/413.01, 413.02, 364/478, 479, 400; 235/375; 221/15, 3; 377/6, 21; 368/10; 206/528, 534, 534.1, 534.2, 538–540, 533

[56] References Cited

U.S. PATENT DOCUMENTS

| | | |
|---|---|---|
| 4,293,845 | 10/1981 | Villa-Reel . |
| 4,361,408 | 11/1982 | Wirtschafter . |
| 4,419,016 | 1/1983 | Zoltan . |
| 4,483,626 | 3/1984 | Noble . |
| 4,504,153 | 3/1985 | Schollmeyer et al. . |
| 4,572,403 | 2/1986 | Benaroya . |
| 4,589,780 | 5/1986 | Takebe . |
| 4,695,954 | 9/1987 | Rose et al. ........................ 364/413.01 |
| 4,725,997 | 2/1988 | Urquhart et al. . |
| 4,747,514 | 5/1988 | Stone . |
| 4,748,600 | 5/1988 | Urquhart . |
| 4,768,176 | 8/1988 | Kehr et al. . |
| 4,768,177 | 8/1988 | Kehr et al. . |
| 4,798,309 | 1/1989 | Stone et al. . |
| 4,823,982 | 4/1989 | Aten et al. . |
| 4,835,372 | 5/1989 | Gombrich et al. . |
| 4,838,453 | 6/1989 | Luckstead . |
| 4,839,806 | 6/1989 | Goldfischer et al. .............. 364/413.02 |
| 4,905,213 | 2/1990 | Masse et al. . |
| 4,911,327 | 3/1990 | Shepherd et al. . |
| 4,916,441 | 4/1990 | Gomrich . |
| 4,962,491 | 10/1990 | Schaeffer ................................ 368/21 |
| 4,970,669 | 11/1990 | McIntosh et al. . |
| 5,012,496 | 4/1991 | Weinreb et al. ........................ 377/21 |
| 5,016,230 | 5/1991 | Seifers et al. . |
| 5,044,516 | 9/1991 | Hoar . |
| 5,047,948 | 9/1991 | Turner . |
| 5,088,056 | 2/1991 | McIntosh et al. . |
| 5,157,640 | 10/1992 | Backner ................................ 368/10 |

*Primary Examiner*—Donald E. McElheny, Jr.
*Attorney, Agent, or Firm*—Hopgood, Calimafde, Kalil & Judlowe

[57] ABSTRACT

Portable programmable medication alarm device for aiding in the administration of medication or pharmaceuticals in accordance with a prescribed medication dosage schedule. In a first illustrative embodiment, the programmable medication alarm device is manually programmed with data representative of a prescribed medication dosage schedule specifying a prescribed administration time, dosage amount, administration route, and medication instructions for each medication dosage to be administered to the patient. In response to the timed occurrence of each programmed administration time, an audible dosage alarm signal is generated and graphical representations of the prescribed administration time, dosage amount, administration route and medication instructions are visually displayed in pre-defined visual display fields. In a second illustrative embodiment, the portable medication alarm device is programmed by loading the prescribed dosage schedule data from a computer system, into the memory of the medication alarm device, using an automated data communication process. Also disclosed is a medication container holder which attaches the programmed medication alarm device to a conventional medication container, such as a eye-drop dispenser bottle, nasal-spray canister or pill bottle, without interfering with the operation thereof.

15 Claims, 13 Drawing Sheets

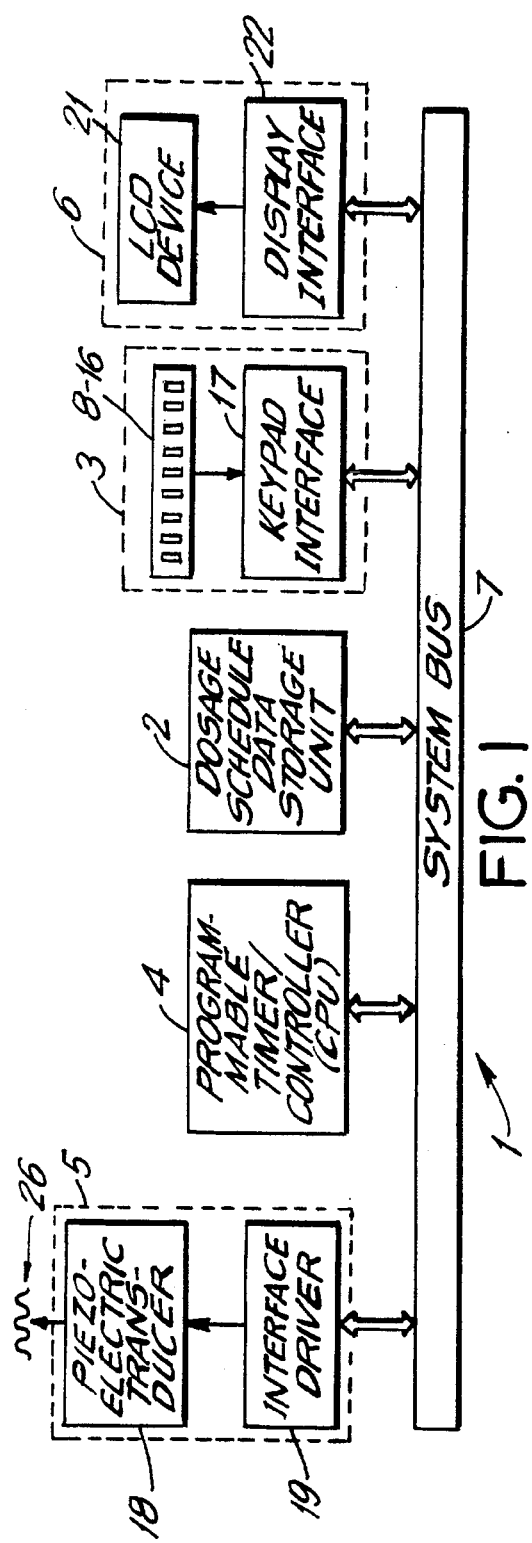
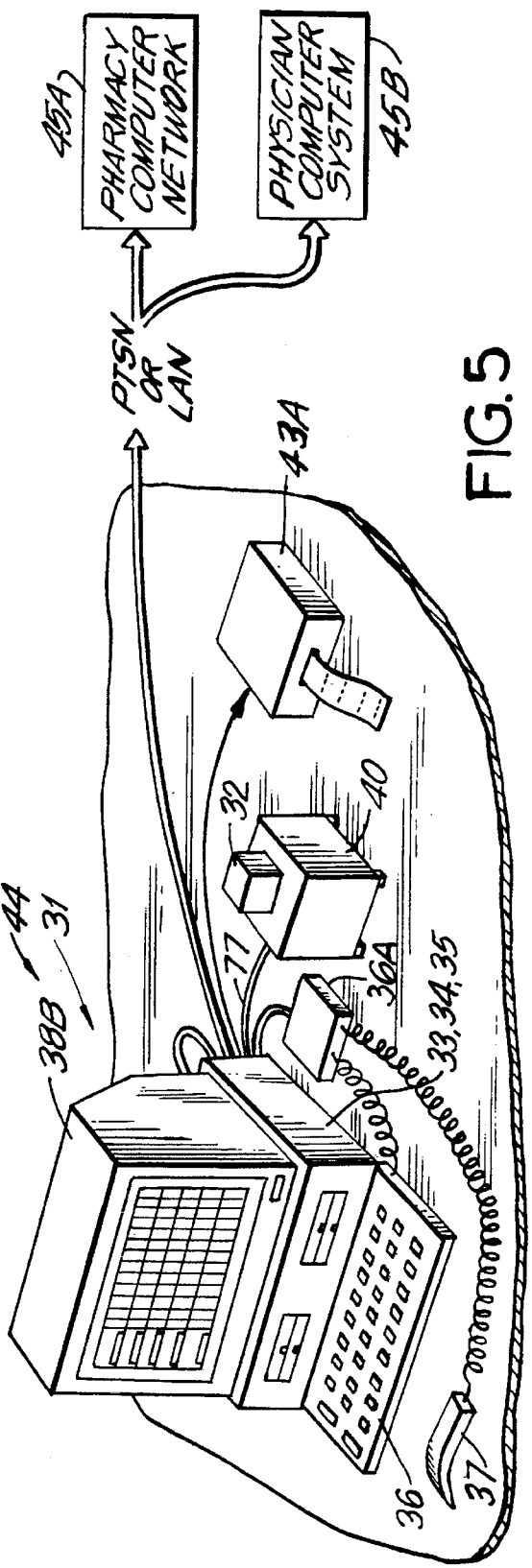

PATIENT: JOHN D. SMITH                PHYSICIAN: FEDERICO MAESTRE, M.D.

| DOSAGE SCHEDULE FRAME NO. | 1 | 2 | 3 | 4 | 5 |
|---|---|---|---|---|---|
| PRESCRIBED TIME OF MEDICATION ADMINISTERED | 8:00 AM | 8:15 AM | 8:30 AM | 9:30 AM | 9:45 AM |
| DOSAGE OF MEDICATION ADM. (IN DROPS) | 2R/1L | 2 DROPS | 2 DROPS | 2 DROPS | 2 DROPS |
| PRESCRIBED ROUTE OF MEDICATION ADMINISTERED | BOTH EYES | RIGHT EYE | RIGHT EYE | RIGHT EYE | RIGHT EYE |
| MEDICATION INSTRUCTIONS | CLOSE 5 MI. | CLOSE 5 MI. | CLOSE 5 MI. | CLOSE 5 MI. | CLOSE 5 MI. |

| DOSAGE SCHEDULE FRAME NO. | 14 | 15 | 16 | 17 | 18 |
|---|---|---|---|---|---|
| PRESCRIBED TIME OF MEDICATION ADMINISTERED | 2:00 PM | 2:30 PM | 3:00 PM | 3:30 PM | 4:00 PM |
| DOSAGE OF MEDICATION ADM. (IN DROPS) | 1 DROP | 1 DROP | 1 DROP | 1 DROP | 1 DROP |
| PRESCRIBED ROUTE OF MEDICATION ADMINISTERED | BOTH EYES | RIGHT EYE | RIGHT EYE | RIGHT EYE | BOTH EYES |
| MEDICATION INSTRUCTIONS | CLOSE 5 MI. | CLOSE 5 MI. | CLOSE 5 MI. | CLOSE 5 MI. | CLOSE 5 MI. |

FIG. 2

MEDICATION: CILOXAN™ OPHTHALMIC SOLUTION

| 6 | 7 | 8 | 9 | 10 | 11 | 12 | 13 |
|---|---|---|---|---|---|---|---|
| 10:00 AM | 10:30 AM | 11:00 AM | 11:30 AM | 12:00 PM | 12:30 PM | 1:00 PM | 1:30 PM |
| 2R/1L | 2 DROPS | 1 DROP | 1 DROP | 1 DROP | 1 DROP | 1 DROP | 1 DROP |
| BOTH EYES | RIGHT EYE | RIGHT EYE | RIGHT EYE | BOTH EYES | RIGHT EYE | RIGHT EYE | RIGHT EYE |
| CLOSE 5 MI. | CLOSE 5 MI. | CLOSE 5 MI. | CLOSE 5 MI. | CLOSE 5 MI. | CLOSE 5 MI. | CLOSE 5 MI. | CLOSE 5 MI. |

| 19 | 20 | 21 | 22 | 23 | 24 | 25 | 26 |
|---|---|---|---|---|---|---|---|
| 4:30 PM | 5:00 PM | 6:00 PM | 7:00 PM | 8:00 PM | 9:00 PM | 10:00 PM | 11:00 PM |
| 1 DROP | 1 DROP | 1 DROP | 1 DROP | 1 DROP | 1 DROP | 1 DROP | 1 DROP |
| RIGHT EYE | RIGHT EYE | RIGHT EYE | RIGHT EYE | RIGHT EYE | RIGHT EYE | BOTH EYES | RIGHT EYE |
| CLOSE 5 MI. | CLOSE 5 MI. | CLOSE 5 MI. | CLOSE 5 MI. | CLOSE 5 MI. | CLOSE 5 MI. | CLOSE 5 MI. | CLOSE 5 MI. |

FIG. 2A

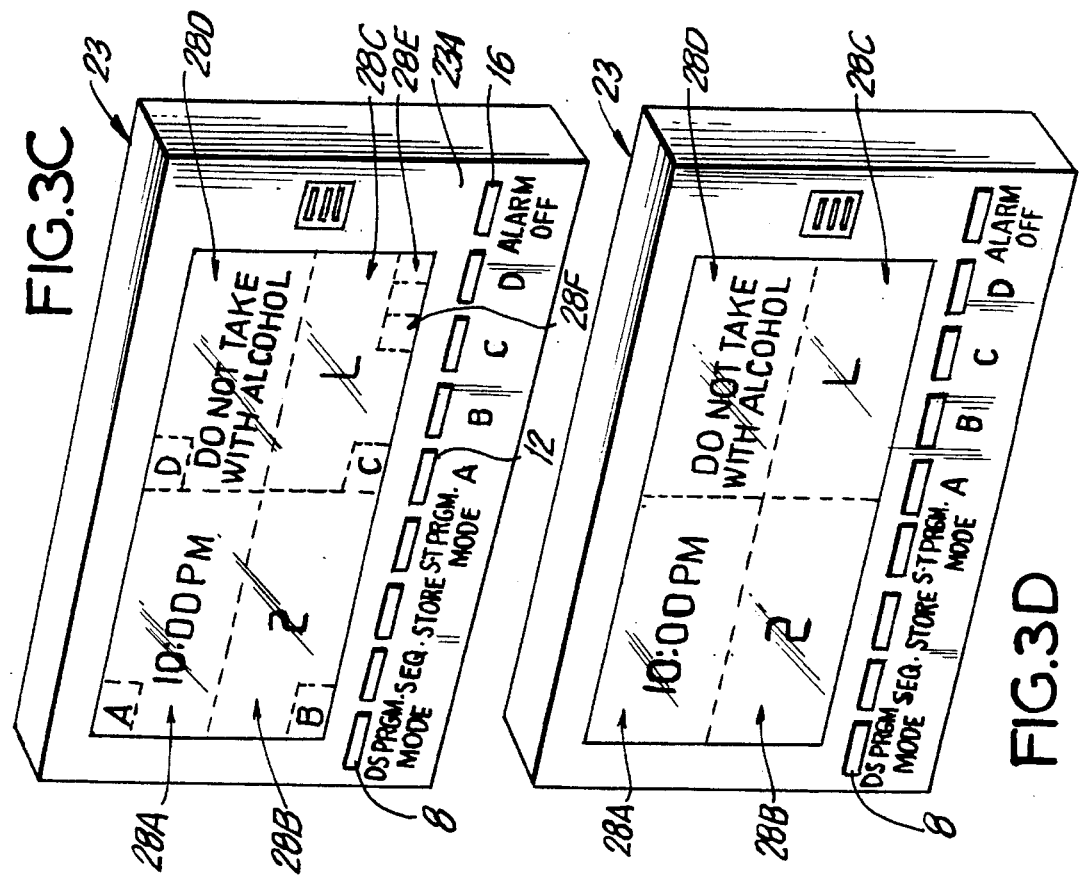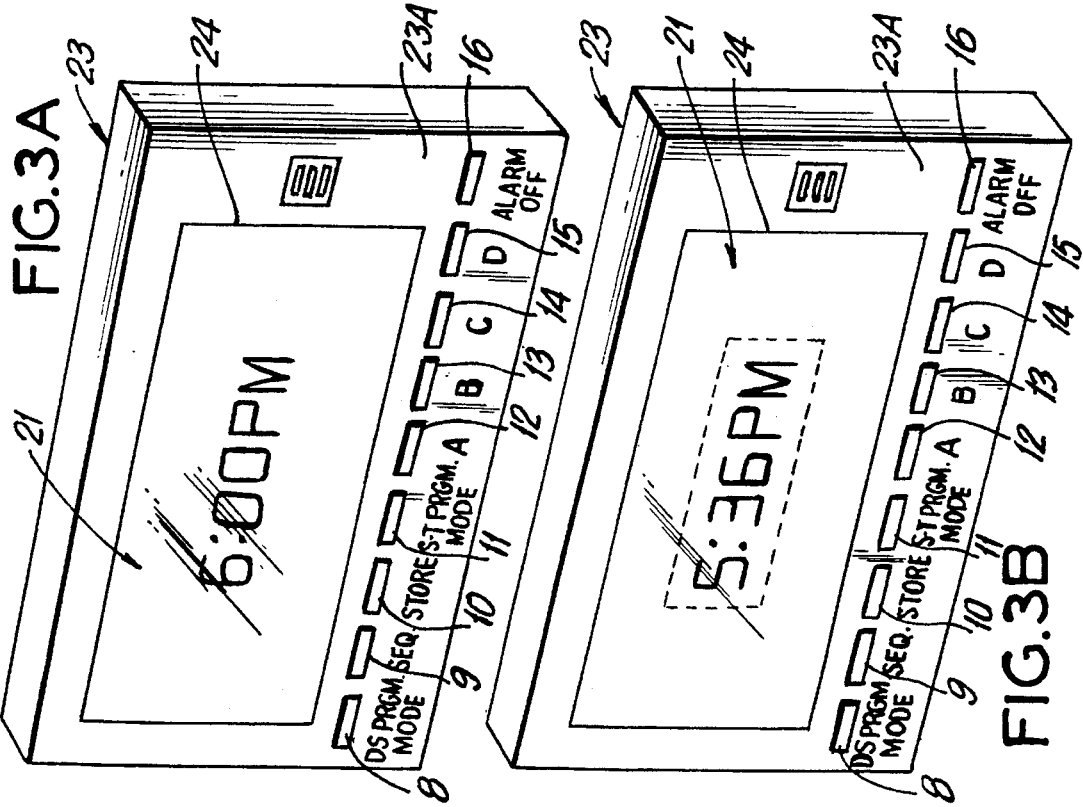

PORTABLE PROGRAMMABLE MEDICATION ALARM DEVICE AND METHOD AND APPARATUS FOR PROGRAMMING AND USING THE SAME

RELATED CASES

This is a continuation of U.S. patent application Ser. No. 07/860,414 entitled "PORTABLE PROGRAMMABLE MEDICATION ALARM DEVICE AND METHOD AND APPARATUS FOR PROGRAMMING AND USING THE SAME" filed Mar. 30, 1992, now U.S. Pat. No. 5,347,453.

BACKGROUND OF INVENTION

1. Field of Invention

The present invention relates to a portable programmable medication alarm device, which facilitates accurate administration of prescribed medications taken by patients.

2. Brief Description of the Prior Art

It is widely recognized that the use of medication in our society has permitted successful treatment of numerous medical conditions. Medical prescriptions written by doctors are typically recorded in computer systems which are linked together in a network accessible by pharmacists. Typically, prescription data in these computer systems is processed using a drug interaction database to determine whether a prescribed medicine is compatible with other forms of prescribed medicine being taken by the patient. If the prescribed medicine is determined compatible, then the prescription is filled and picked up or delivered to the patient at home.

Presently, dosage instructions are printed on medication bottles. However, there are thousands of medications, such as eye drops, ear drops and nasal spray, which often require complex dosage schedules having dosage levels, administration routes and instructions that may change for each specific time of administration. While the physician will often provide the patient with a written dosage schedule, patient's frequently forget to use their medications as prescribed or confuse the frequency which their medications are to be used.

In order to facilitate accurate use of prescribed medications, a number of programmable medication alarm devices have been proposed, for example, in U.S. Pat. Nos. 5,088,056; 5,016,230; 4,970,669; 4,942,544; 4,905,213; 4,768,176; 4,419,016; 4,367,955; 4,483,626; and 4,837,719. In general, while prior art medication alarm devices are capable of reminding the patient of specific times that medication is to be taken during the day, they suffer from several significant shortcomings and drawbacks.

In particular, while U.S. Pat. No. 4,504,153 discloses a method for automatically programming a medication alarm device, this prior art device fails to provide patients with complete instructions required with prescription medications having different dosage levels and delivery routes at different times of administration.

In addition to providing inadequate instructions, other prior art devices are generally difficult to program and pose a high likelihood of dosage schedule programming errors.

Consequently, the prior art has not provided an easily programmable, portable medication alarm device which facilitates accurate administration of virtually any prescribed medication to be taken by a patient.

Accordingly, it is a primary object of the present invention to provide a portable programmable medication alarm device which visually displays the prescribed dosage level, delivery route and medication instructions for each specific time of medication administration that has been programmed in accordance with a dosage schedule prescribed by a doctor or pharmacist.

It is another object of the present invention to provide such a portable medication alarm device, in which the prescribed medication dosage schedule is manually programmed using predefined visual display fields, an audible alarm signal is generated upon the timed occurrence of each programmed time of medication administration, and in response thereto, a graphical indication of the programmed dosage level, delivery route and patient instructions are visually displayed for the patient to easily read and follow.

Another object of the present invention is to provide such a medication alarm device, in which the prescribed medication dosage schedule is programmed using a computer system, an audible alarm signal is generated upon the timed occurrence of each programmed time of medication administration, and in response thereto, a graphical indication of the programmed dosage level, delivery route and patient instructions are visually displayed for the patient to easily read and follow.

Another object of the present invention is to provide a medication compliance system which comprises a portable programmable medication alarm device and a computer system for programming the medication alarm device with a prescribed dosage schedule by way of automated data communications operations.

A further object of the present invention is to provide a programming interface unit for use with a conventional computer system, and which permits a prescribed medication schedule stored in memory of the computer system, to be readily loaded into a programmable medication alarm device.

It is another object of the present invention to provide a portable medication alarm device which can be releasably fastened to any medication container, programmed with a medication dosage schedule using a computer system and then carried by the patient so that he or she is reminded of when the medication should be taken, in what dosage and along what delivery route.

It is yet another object of the present invention to provide a medication container holder in which the programmable medication alarm devices of the present invention can be simply installed, and in which a conventional eye drop, nasal spray or other medication dispenser can be received while permitting the dispensing of prescribed medication dosages in a conventional manner.

These and other objects of the present invention will become apparent hereinafter.

BRIEF DESCRIPTION OF THE DRAWINGS

For a more complete understanding of the objects of the present invention, the Detailed Description of the Illustrative Embodiments is to be taken in connection with the following drawings, in which:

FIG. 1 is a system block diagram of a manually-programmable medication alarm device according to the present invention;

FIGS. 2 and 2A are a schematic diagram of an exemplary medication prescription which can be programmed into the alarm devices of the present invention;

FIG. 3A is a perspective view of the manually-programmable medication alarm device hereof shown operating in its standard-time display mode, displaying only the standard time on the visual display;

FIG. 3B is a perspective view of the manually-programmable medication alarm device hereof, shown operating in its standard-time programming mode, visually displaying a standard time to be set;

FIG. 3C is a perspective view of the manually-programmable medication alarm device hereof, shown operating in its dosage schedule programming mode, visually displaying administration time data, dosage amount data, delivery route data and other patient instruction data associated with the frame of a prescribed medication dosage schedule being programmed;

FIG. 3D is a perspective view of the manually-programmable alarm device hereof, shown operating in its alarm display mode, visually displaying administration time data, dosage amount data, delivery route data and other medication instruction data associated with the dosage of medication to be taken at the displayed administration time;

FIG. 5 is a perspective view of the pharmacy computer system of the present invention, in which a computer-programmable medication alarm device of the present invention is shown inserted into the programming interface unit of the pharmacy computer system, for dosage schedule programming;

DETAILED DESCRIPTION OF THE ILLUSTRATIVE EMBODIMENTS

Figure 4:
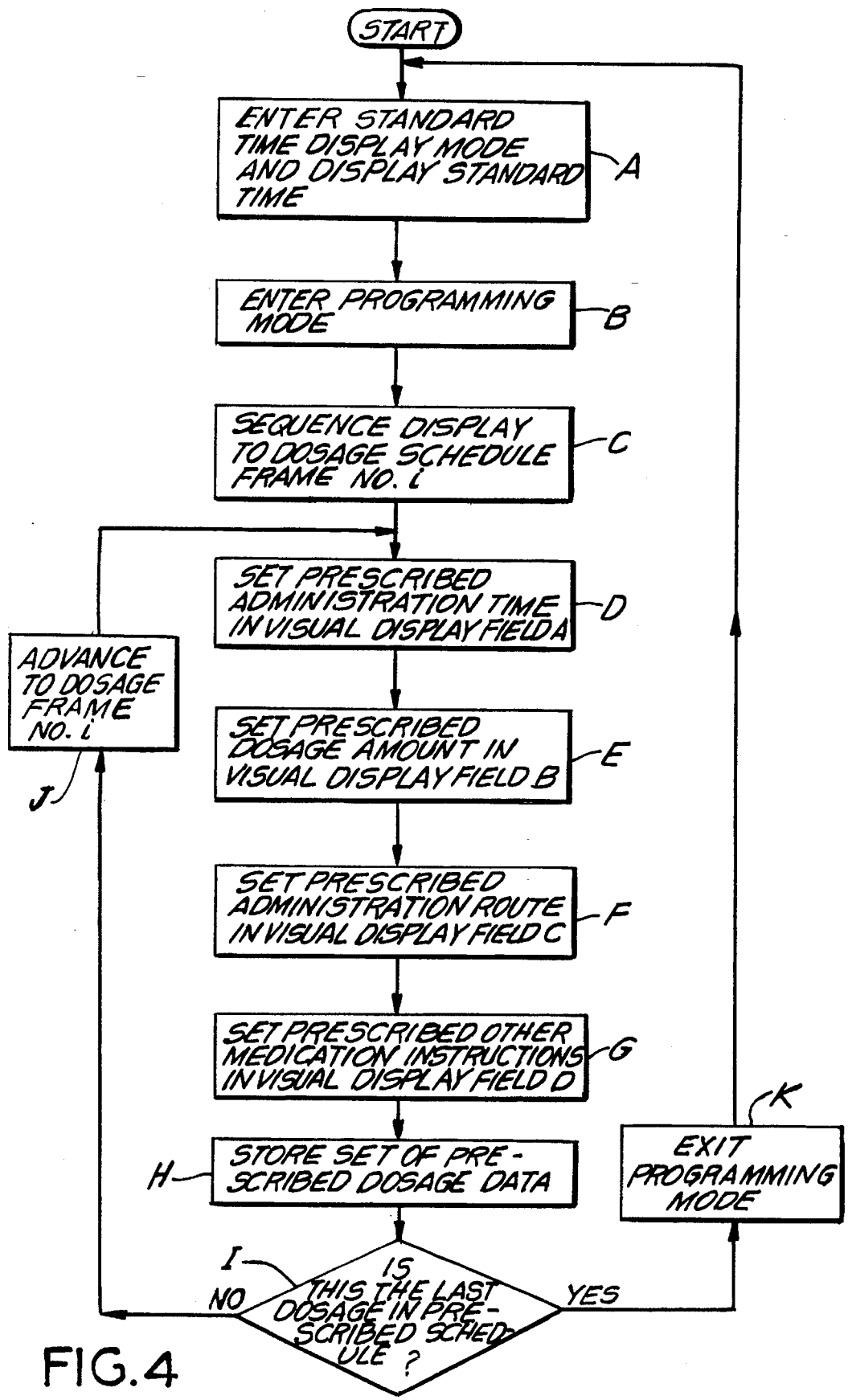
FIG. 4 is a flow chart illustrating the steps involved in programming the manually-programmable medication alarm device of the illustrative embodiment of the present invention.

Referring now to the drawings wherein like reference numbers designate similar parts through the various views, attention is first directed to FIGS. 1 through 3 in which the manually-programmable medication device hereof is described.

As illustrated in FIG. 1, medication alarm device 1 comprises a number of system components, namely: dosage schedule data storage unit 2 for storing frames of dosage schedule data of one or more graphically displayable prescribed dosage schedules; dosage schedule programming unit 3 for manually programming data frames of a prescribed graphical dosage schedule and the standard-time to be measured by the medication alarm device; programmable timer/controller 4 for maintaining accurate measurement of standard-time and programmed administration times and for performing various programming and control functions in accordance with a microcode control program (not shown); alarm signal generating unit 5 for generating an audible alarm signal; and dosage schedule display device 6 for displaying standard-time and frames of programmed dosage schedule data upon generation of the audible alarm signal. As illustrated, data storage unit 2, programming unit 3, alarm signal generating unit 5 and display device 6 are operably associated with programmable timer/controller 4 by way of system bus 7.

In the illustrated embodiment, programming unit 3 comprises a plurality of programming keys 8 through 16 and associated interface circuitry 17. Alarm signal generating unit 5 comprises a piezoelectric transducer 18 and associated interface and driver circuitry 19. In addition, display device 6 comprises a liquid crystal display (LCD) device 21 and associated display interface circuitry 22.

While not shown to avoid obfuscation of the present invention, battery power circuitry is provided in a manner well known in the electronic timer art. In a preferred embodiment, these system components are realized as an integrated microelectronic circuit using VLSI semiconductor technology well known in the electronic circuit fabrication art. To indicate when the miniature battery source (e.g. 1.5 volt) used in the circuit, should be replaced, a battery level detection circuit (not shown) is also provided in the integrated microelectronic circuit. In alternative embodiments of the present invention, the power source may be realized as a photovoltaic circuit (e.g. solar cell) and associated circuitry well known in the electronic art.

As illustrated in FIGS. 3A through 3D, the microelectronic circuitry and associated components of programmable medication alarm device 1 are housed in a thin, wafer-like casing 23. The casing has a hollow cavity for containing the microelectronic circuit board on which system components of the first illustrative embodiment are realized. As shown, casing 23 has a window 24 through which LCD device 21 can be viewed. A plurality of spaced apart apertures formed in the front (i.e. face) panel of the casing 23 permits programming keys 8 through 16, to project slightly therethrough. In order that acoustical energy of the dosage alarm signal can emanate towards the patient with minimal damping, perforations 25 are formed in front panel 23A.

Preferably data storage unit 2 comprises an erasable electronic programmable data storage device (e.g. EEPROM) or functionally equivalent element, which is capable of storing digitally encoded data of graphical information contained in the prescribed medication dosage schedule. In the illustrative embodiment of the invention, manually depressible keys 8, 9, 10, 12, 13, 14 and 15 and associated interface circuitry 17 of programming unit 3, permit the physician, pharmacist (or even patient) to enter dosage schedule data into data storage unit 2 under the control of programmable timer/controller 4. Keys 11 and 12, on the other hand, facilitate programming of the standard-time, whereas key 16 facilitates deactivation of the dosage alarm signal. As will be described in detail hereinafter, each depressible key is assigned a particular programming or control function which is carried out by programmable medication alarm device 1.

In FIGS. 2 and 2A, an exemplary medication prescription 26 is schematically illustrated in accordance with the present invention. In general, the medication prescription comprises graphical information 26A specifying (i) the name of the patient, the name of the attending physician and the medication being prescribed and (ii) a prescribed dosage schedule indicated by reference numeral 26B. As shown, prescribed dosage schedule 26B comprises data specifying a prescribed time, a prescribed dosage amount and a prescribed administration route for each medication dosage to be administered to the patient during a particular time period (e.g. a day, several days, weeks or months, etc). In addition, the prescribed dosage schedule includes medication instructions relating to administration directions, patient warnings and other requirements which, when followed by the patient, assure safe and effective use of the prescribed medication.

In order to fully appreciate the present invention as it is described hereinafter, it is appropriate to discuss at this juncture, one particular problem in the field of ophthalmology which the medication alarm device of the present invention solves in a simple and effective manner.

One of the most devastating and sight threatening diseases in the eye is the corneal ulcer. The cornea is the clear most exposed surface of the eye. Daily we are exposed to hundreds of bacteria and pathogens that invade the surface of the eye. While our eyes are equipped with a mechanism to expel debris and protect the cornea from infections, there has been a steep increase in the incidence of corneal ulcers in the past twenty years, especially with the introduction of daily and extended wear soft contact lenses. If a corneal ulcer is not correctly treated in the first hours of development, complications can arise, resulting in loss of vision or total loss of the eye. The major problem in the treatment of this eye disease is that the cornea is comprised of avascular tissue. Consequently, antibiotics administered by oral or parental methods will not reach the site of infection. In this case, the topical route is the most effective way to treat the corneal ulcer. However, the sole drawback associated with topical administration of antibiotics is that frequent and uninterrupted administration of the antibiotic must be achieved in order to have adequate penetration and coverage. Hitherto, one of the primary reasons for unsuccessful therapy of the corneal ulcer has been poor medication compliance, and its consequence in many patients has been total loss of the eye.

Treatment of medical disorders such as the corneal ulcer using the programmable medication alarm device of the present invention, is best appreciated by considering the case in which a 34 year old male, who is daily wearer of contact lenses, went skiing for a weekend. Upon discovering he forgot his lens case, he decided to sleep with the lenses in his eyes all weekend. On Sunday morning, after spending a few hours in a hot tub the previous evening, he develops sudden bilateral ocular pain with redness and blurred vision. Upon arrival to the nearest ophthalmologist, he is diagnosed with a corneal ulcer in his right eye and a corneal abrasion in his left eye. His right eye needs immediately a high concentration of antibiotics, while his left eye needs to be treated for a regular corneal scratch. The prescribed medication is Ciloxan™ which is a broad spectrum antibiotic. The medication dosage schedule prescribed for the first day of treatment is illustrated in FIGS. 2 and 2A. Typically, the dosage schedule for the second day of treatment will involve administering the ophthalmic drops every hour on the right eye and four times a day on the left eye. If the prescribed therapy is successful, the medication treatment is continued for ten days using the second day dosage schedule.

Compliance with this prescribed dosage schedule has been extremely difficult for the patient, owing to its inherent complexity. Also, owing to the inherent limitation of prior art medication alarm devices, it has been virtually impossible to use such devices in facilitating compliance with such dosage schedules, in particular. However, as will be illustrated hereinafter, compliance with dosage schedules of arbitrary complexity can now be simply achieved using the programmable medication alarm device of the present invention.

Once the dosage schedule data has been programmed (e.g. stored) in data storage unit 2 by a programming procedure to be described hereinafter, the programmable timer/controller 4, under its control program, utilizes prescribed time data stored in data storage unit 2 to time (i.e. meter) the occurrence of each prescribed administration time specified in the programmed dosage schedule. In order to carry out this function, programmable timer/controller 4 also includes one or more clock-pulse oscillators for generation of clock pulses at predetermined frequencies. These clock pulse oscillators, in cooperation with clock pulse storage registers, comparitors, multiplexers, digital logic and control circuitry provides a programmable clock for counting standard-time as well as the timed occurrence of programmed administration times. In a manner well known in the horological art, standard-time is timed by counting clock pulses within a counting system capable of metering the time elapsing within a predetermined time period, such as a calendar year. Timing the occurrence of each programmed administration time can be achieved by comparing (i) the digital bit sequence associated with each time instant being measured by the standard-time clock, and (ii) the digital bit sequence associated with each programmed administration time. When a match is detected between such digital bit sequences, indicative of the timed occurrence of a programmed administration time, a control signal is then generated by the programmable timer/controller and is used to generate an audible dosage alarm signal, as will be described in greater detail below.

Programmable timer/controller 4 provides the user several options with respect to administration time programming. For example, the user may program administration times according to repetitive fixed interval timing (e.g. every 2.5 hours), or according to variable interval timing (e.g. at 6:30 AM, at 6:45 AM, at 7:30 AM, at 9:15 AM, at 12:00 AM, at 3 PM, at 6 PM, etc). This feature provides the doctor or pharmacist full flexibility when prescribing dosage schedules for particular medications.

In a conventional manner, programmable timer/controller 4 continuously keeps track of the standard-time and visually displays the same on LCD display screen 21. Upon the timed occurrence of each administration time specified in the programmed dosage schedule, the programmable timer/controller generates a control signal which is provided to alarm signal generating unit 5 by way of system bus 7. In response to the generation of this control signal, a number of events occur in accordance with the system control program running within the programmable timer/controller. First, the control signal is detected by interface/driver circuitry 19 which generates an electrical signal that is provided to piezoelectric transducer 18. In response to the electrical signal, piezo-electric transducer 18 generates an acoustical alarm signal which is perceptible to the patient who is in possession of the programmed medication alarm device of the present invention. However, in other embodiments, the alarm signal may be realized by generating any form of energy or disturbance which the patient can perceive.

Upon generation of the dosage alarm signal, the programmable timer/controller accesses dosage schedule data stored in data storage unit 2. The accessed data is then provided to display interface circuitry 22. The display interface circuitry generates signals which are provided to LCD device 21 so as to graphically display in accordance with the programmed dosage schedule, the prescribed administration time, dosage amount, administration route and medication instructions for the prescribed medication. When hearing the alarm signal, the patient is reminded to comply with the prescribed dosage schedule frame being visually displayed on the display surface of the LCD device.

Having described the structure and function of the manually-programmable medication alarm device of the present invention, its various modes of operation will now be described with reference to FIGS. 3A through 3D. For simplicity of operation, manually-programmable medication alarm device 1 is provided with four primary modes of operation, namely: a standard-time display mode illustrated in FIG. 3A; a standard-time programming (and review) mode illustrated in FIG. 3B; a dosage schedule programming mode illustrated in FIG. 3C; and a dosage alarm mode illustrated in FIG. 3D.

The standard-time display mode is entered by pressing key 8, indicated by "DS PRGM. MODE" on the casing front panel 23A shown in FIG. 3A. When this mode is entered, only the standard-time is displayed on the visual display screen of the LCD device. When it is desired to program the standard-time, the standard-time programming mode is entered by depressing key 11 indicated by "S-T PRGM. MODE" on the casing front panel as illustrated in FIG. 3B. The desired standard-time is selected by depressing key 12, indicated by "A" on the casing front panel illustrated in FIG. 3B. When the desired standard-time is reached, key 12 is released. To set the selected standard-time, key 11 is depressed once again, whereupon the medication alarm device is automatically returned to the standard-time display mode, as shown in FIG. 3A.

When it is desired to exit the standard-time display mode of FIG. 3A and enter the dosage schedule programming mode of FIG. 3C, key 8 is pressed once again. This key operation causes the medication alarm device to enter the dosage schedule programming mode in which prescribed items of graphical dosage schedule data are programmed for display in visual display fields 28A through 28D upon the timed occurrence of corresponding medication administration times.

In the dosage schedule programming mode, items of dosage schedule data are displayed in their respective visual display fields illustrated in FIG. 3C, for selection and subsequent storage in memory 2. The data contained in visual display fields represents a single frame of the dosage schedule data associated with a single dosage of medication to be administered in a particular amount, at a particular time and in a particular manner. In the dosage schedule programming mode, each frame of dosage schedule data is indexed by a frame number (e.g. i=1, 2, 3, 4, ... ) displayed in visual display field 28E, illustrated in FIG. 3C. By pressing key 9, indicated by "SEQ" on the casing front panel, frames of the dosage schedule are sequenced from i=1, 2, 3 ... N, where N can be any integer. In some applications, N may be 4 or greater to provide at least four programmable administration times during a 24 hour day. In other applications, N may be at least 64 or greater to provide at least sixty-four programmable administration times during a single 24 hour period. In the illustrative embodiment of the manually-programmable medication alarm device, the frames of dosage schedule data are associated with a single 24-hour day, although in other embodiments, these frames can extend over a period of days, weeks or months. In such extended-time period programming, it may be desired to display on the LCD device during the programming mode, a weekly or monthly calendar which facilitates dosage schedule programming.

In order to set the prescribed administration time for a particular frame in a prescribed dosage schedule, key 12 indicated by "A" on the casing front panel is depressed. While key 12 is depressed, the time displayed in visual display field 28A is sequentially incremented in a module manner, in increments of minutes. When the prescribed administration time is reached, key 12 is released.

The prescribed dosage amount is set by depressing key 13 indicated by "B" on the casing front panel. While key 13 is depressed, the possible dosage amounts are sequentially displayed in visual display field (e.g. 1, 2, 3, 4, 1L/1R, 2L/1R, 3L/1R, 4L/1R, 1L/2R, 1L/3R . . . etc.). When the prescribed dosage amount is reached, key 13 is released. In ophthalmic medication applications, the displayed dosage number or number pair may represent the number of eye drops to be administered to the patient's eyes. In other applications, the displayed dosage number may represent the number of discharges of nasal spray to be administered into the patient's nostrils, or possibly the number of pills or units of prescribed medication to be taken by the patient.

Similarly, the prescribed administration route is set by depressing key 14 indicated by "C" on the casing front panel. Each time key 14 is depressed, the possible medication delivery routes are sequentially displayed in visual display field 28C (e.g. L, R, LR, L, R, LR, L . . . ). When the prescribed delivery route is reached, key 14 is released. In ophthalmic medicine applications, the displayed character(s) in visual display field 28C may represent the eye in which the prescribed dosage of eye drops is to be administered. The displayed character "L" can represent that the left eye is the prescribed route of administration, whereas the displayed character "R" can represent that the right eye is the prescribed route of administration. When characters "L" and "R" are both displayed, each eye should receive the prescribed dosage of eye drop medication being simultaneously displayed. In other applications, the displayed character(s) may represent in which nostril (i.e. left, right or both) the displayed medication dosage should be administered.

For safe and effective medical treatment to occur, many prescription medications require compliance with other instructions. For example, some medications should be taken with plenty of water, after meals and/or in the absence of alcohol. In some ophthalmic applications, the patient's eyes should be closed for a particular period of time after administration of ophthalmic solution. In such medication applications, one or more medication instruction (e.g. directions, patient warnings, etc.) will be displayed in visual display field 28D of LCD device 21. Such medication instructions may be expressed in either a text format or by way of graphical icons that are simply understood by the patient. Data representative of such medications instructions is programmed into storage unit 2, along with other items of data contained in the prescribed medication dosage schedule. Such medications instructions are set in manually-programmable medication alarm device 1 by depressing key 15 indicated by "D" on the casing front panel. Each time key 15 is depressed, possible patient instructions are sequentially displayed in visual display field 28D (e.g. "TAKE WITH WATER"; "DO NOT TAKE WITH ALCOHOL"; "TAKE WITH FOOD"; "CLOSE EYES FOR 5 MINUTES"; "TAKE WITH WATER" . . . etc.). When the prescribed patient instruction(s) is reached, key 15 is released. Then, after each prescribed frame of a prescribed dosage schedule has been selected in a manner described above, the data frame is stored in memory 2 by depressing key 10 two times. At this time, frame index i is automatically incremented by 1 for the programming of the subsequent frame of the dosage schedule.

After exiting the dosage-schedule programming mode by pressing key 8 the medication alarm device returns to its standard-time display mode illustrated in FIG. 3A. Whenever the standard-time equals a programmed administration time, the dosage alarm mode is automatically entered. In response, programmable timer/controller 4 generates a control signal in response to which the patient alarm signal is generated. Simultaneously, the programmed items of dosage schedule data associated with this administration time, are displayed in visual display fields 28A, 28B, 28C and 28D of the LCD device. To stop the alarm signal, the user depresses key 16 indicated as "ALARM-OFF" on the casing front panel. Thereupon, programmable timer/controller 4 displays a " " mark in visual display field 28F illustrated in FIG. 3C. This mark is stored in memory 2 and is displayed at a later time in the dosage schedule display mode, to inform the patient (or pharmacist) that the prescribed dosage of medication has been taken in accordance with the programmed dosage schedule. After reading the display screen and administering the prescribed dosage of medication, the device can be returned to standard-time display mode by depressing key 8. At any time, the patient may review programmed frames of dosage schedule data by depressing key 8 to enter the dosage schedule programming mode, and then selectively sequencing through the data frames by depressing key 9. Depressing key 8 will return the device to the standard-time display mode.

Referring to FIGS. 3A through 4, a method of manually programming medication alarm device 1 of the present invention will now be described.

As illustrated in FIGS. 2 and 2A, a prescribed medication dosage schedule to be programmed into medication alarm device 1, typically comprises a plurality of frames of graphical dosage schedule data, in which each frame corresponds to a single dosage of medication. Each frame of graphical data is programmed (i.e. set) in the medication alarm device by carrying out the steps described in blocks A through H of FIG. 4.

As indicated in Block A of FIG. 4, the manually-programmable medication alarm device is normally in its standard-time display mode, displaying only the standard-time as shown in FIG. 3A. As indicated in Block B, the dosage schedule programming mode is then entered by pressing key 8, generating the display shown in FIG. 3C. As indicated in Block C, the first dosage schedule data frame is accessed from memory 2 by pressing key 9 and causing frame No. 1 to be displayed in visual display field 28E. As indicated in Block D, the prescribed administration time for dosage No. i=1 (i.e. frame i=1) is selected by depressing key 12 long enough to display the prescribed administration time in visual display field 28A. As indicated in Block E, the prescribed dosage amount is set in memory for dosage No. i=1 by depressing key 13 as required to display the prescribed dosage amount in visual display field 28B. As indicated in Block F, the prescribed administration route for dosage No. i=1 is selected by depressing key 14 as required to display the prescribed route in visual display field 28C. As indicated in Block G, the prescribed medication instructions for dosage No. 1 is selected by depressing key 15 to display the medication instructions in visual display field 28D. After this frame of graphical data has been selected, then the selected dosage schedule data frame is stored in memory 2 by pressing key 10, as indicated in Block H.

As indicated at Block I, dosage schedule data frame No. i=2 is accessed by depressing key 9, whereupon index i=2 is displayed in visual display field 28E. Data items in frame No. i=2 are set by carrying out Blocks D through H, in a manner described above. When the last frame of dosage schedule data has been set, then as indicated at Block K, the dosage schedule programming mode is exited by depressing key 8. This automatically returns the medication alarm device to its standard-time display mode shown in FIG. 3A.

The manually-programmable medication alarm device described above can be modified so that it can be automatically programmed using a data storage and processing device, which obviates the manual entering of prescribed dosage schedule data into the medication alarm device of the present invention. According to this embodiment of the invention, the data storage and processing device in the form of a computer system 31 can be provided at a pharmacy counter, for example, in order to automatically program medication alarm device 32 with a prescribed dosage schedule, as shown in FIGS. 2 and 2A, that has been formulated by a physician at a remote location or by a pharmacist locally situated.

Figure 6:
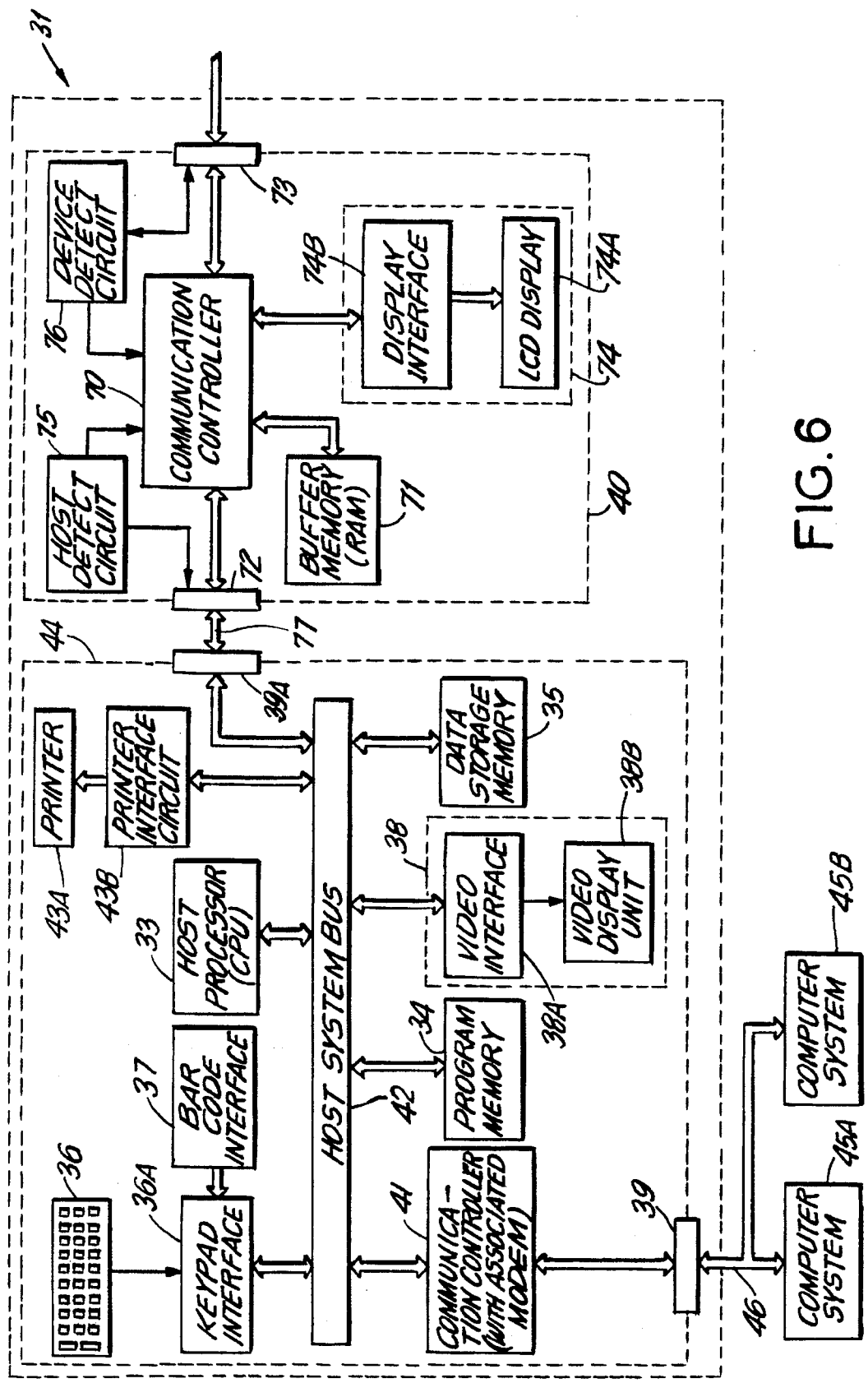
FIGS. 6 and 6A are a system block diagram of the pharmacy computer system shown operably connected to the computer-programmable medication alarm device as illustrated in FIG. 5.
Figure 6A:
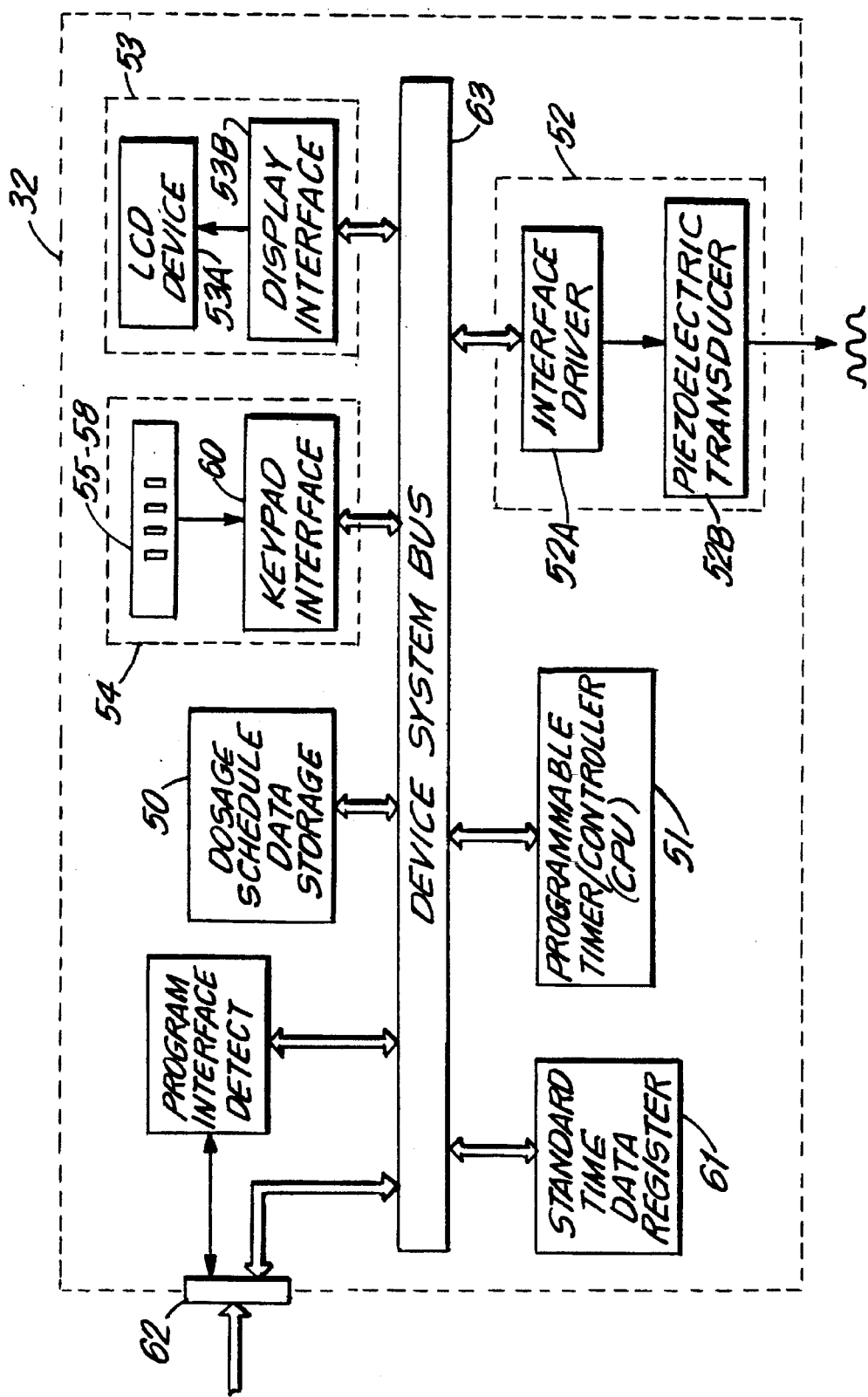

As illustrated in FIGS. 6 and 6A, pharmacy computer system 31 comprises a number of system components, namely: host processor 33 (e.g. CPU or microprocessor); program memory 34; data storage memory 35; data entry devices such as keyboard 36, bar-code symbol reading device 37 and a keyboard wedge interface 36A operably associated therewith; visual display unit 38 comprising video interface 38A and color video display device 38B; data communication ports 39 and 40 operably associated with host processor 33; communication processor (with associated modem) 41 interfaced with data communication port 39; a programming interface unit 40 operably associated with data communication port 42; and a high resolution printer 43A operably associated with host processor 33 by way printer interface circuitry 43B. As illustrated, system components are operably associated with host processor 33 by way of host system bus 42, to provide a computer workstation 44 shown in FIG. 5.

Preferably, data communication port 39A is adapted to support a RS-232 or other serial-data protocol for programming medication alarm device 32 of the present invention. Similarly, data communication port 39 is preferably adapted to support a RS-232 or other serial-data protocol. In this way, pharmacy computer system 31 can transmit and receive prescription and related data among other pharmacy computer system(s) 45A, or with remotely situated computer system(s) 45B which can be operated by a physician who desires to prescribe medications which are to be filled using the pharmacy computer system of the present invention. Data communication among such computer systems can be conducted over a data communication link 46 which may be realized using a public telecommunication switching network (PTSN), a local area network (LAN), or any other suitable data communication medium.

As illustrated in FIGS. 6 and 6A, the computer-programmable medication alarm device 32 comprises a number of system components, namely: dosage schedule data storage unit 50 for storing frames of graphical dosage schedule data and related prescription data; programmable timer/controller 51 for maintaining accurate measurement of standard-time and programmed administration times and for performing various programming, control and communication functions in accordance with a microcode control program (not shown) contained therein; alarm signal generating unit 52 including associated interface/driver circuitry 52A and piezoelectric transducer 52B for generating an audible alarm signal; dosage schedule display unit 53 comprising LED device 53A and associated display interface circuitry 53B for displaying standard-time and frames of programmed dosage schedule data upon the generation of the audible alarm signal; user control selection unit 54 including manually-depressable control keys 55 through 58 and associated interface circuitry 60; a standard-time data register 61 for buffering updated standard-time data; and a data communication port 62 through which digitized graphical and other data can be passed between the medication alarm device and an external data communication processor interfaced therewith. As illustrated, data storage unit 50, control selection unit 54, alarm generating unit 52, display device 53, data register 61 and data communication port 62 are each operably associated with programmable timer/controller 51 by way of system bus 63. While not shown, battery power circuitry and battery level detection circuitry are provided in a manner well known in the art. Also, programmable timer/ controller has a program memory for storage of a control program (e.g. microcode) that governs the operation of the medication alarm device. As in the first embodiment, these system components are preferably realized as an integrated microelectronic circuit using VLSI semiconductor technology.

Figure 8A:
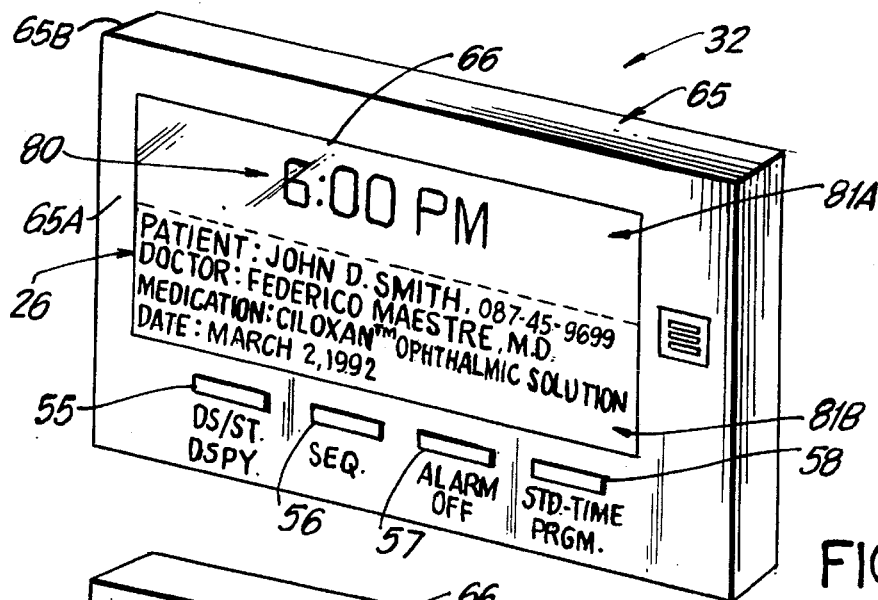
FIG. 8A is a perspective view of the computer-programmable medication alarm device shown operating in its standard-time display mode, visually displaying the standard-time on the upper display field of the visual display and patient, physician, and prescribed medication information in the lower display field thereof.
Figure 8B:
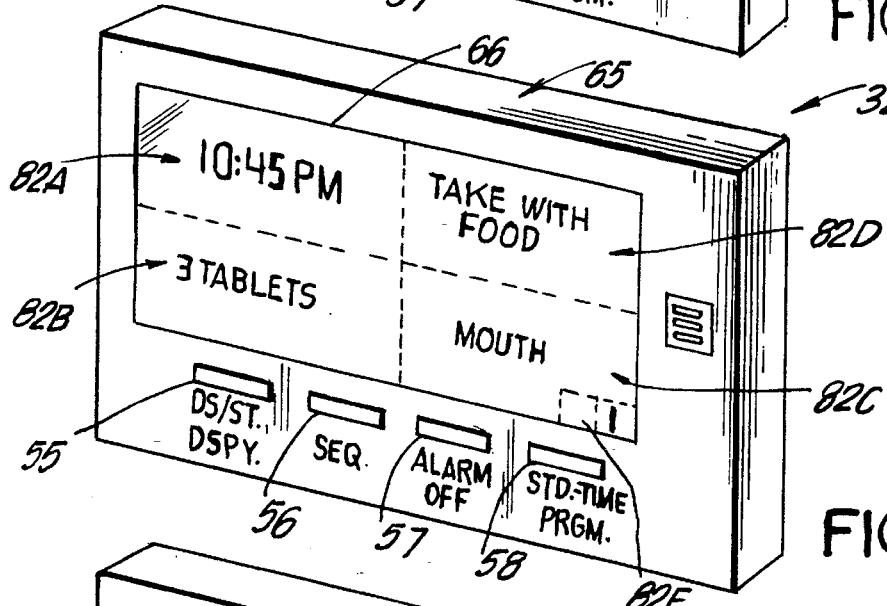
FIG. 8B is a perspective view of the computer-programmable medication alarm device shown operating in its dosage schedule display mode, visually displaying a frame of administration time data, dosage amount data, delivery route data, and other medication instruction data in the programmed medication dosage schedule.
Figure 8C:
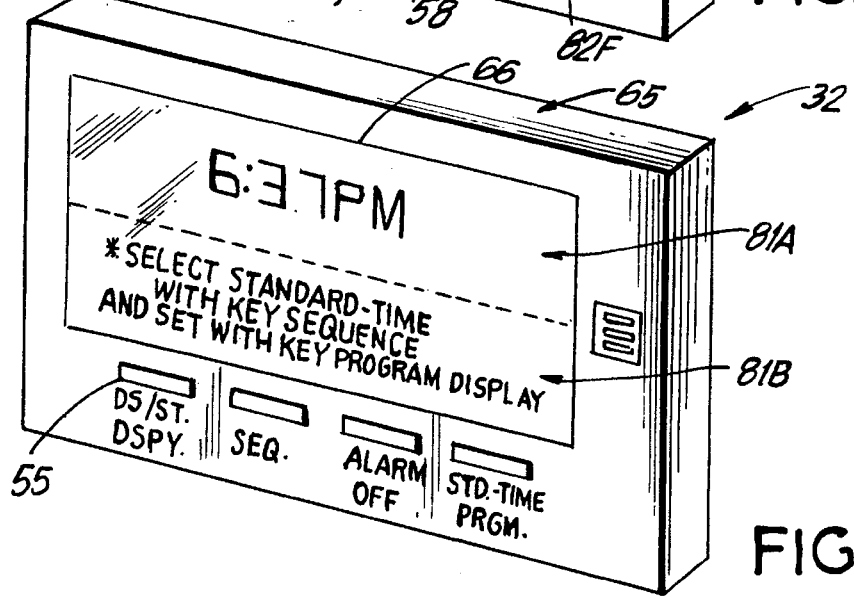
FIG. 8C is a perspective view of the front panel of the computer-programmable medication alarm device shown operating in its standard-time programming mode, visually displaying a selected standard-time to be set.

As illustrated in FIGS. 8A through 8C, the microelectronic circuitry and associated components of programmable medication alarm device 32 are housed in a thin, wafer-like casing 65. The casing has a hollow cavity for containing the microelectronic circuit board on which system components of the second illustrative embodiment are realized. As shown, casing 65 has a window 66 through which LCD device 53B can be viewed. A plurality of spaced apart apertures formed in the front panel of the casing permits control selection keys 55 through 58 to project slightly therethrough. As will be described in greater detail hereinafter, control selection keys 55 through 58 permit the pharmacist and patient to (i) selectively review the prescribed dosage schedule programmed into the medication alarm device; (ii) deactivate the alarm signal generator when it is activated; and (iii) manually program the standard-time if and when desired. In order that acoustical energy of the dosage alarm signal can emanate towards the patient with minimal damping, perforations 67 are formed in casing front panel 65A as shown.

Figure 7:
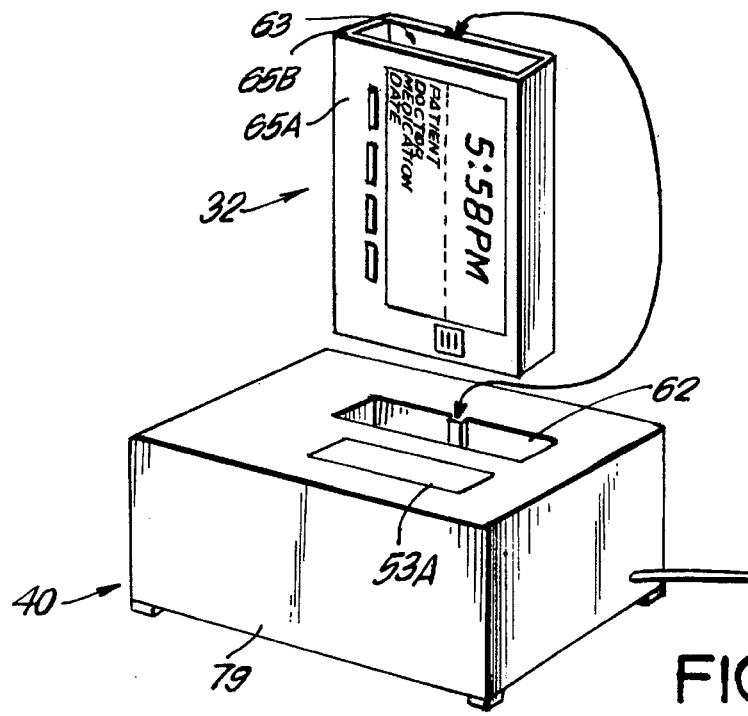
FIG. 7 and 7A are perspective views showing the computer-programmable medication alarm device being inserted into the programming interface unit for dosage schedule programming.
Figure 7A:
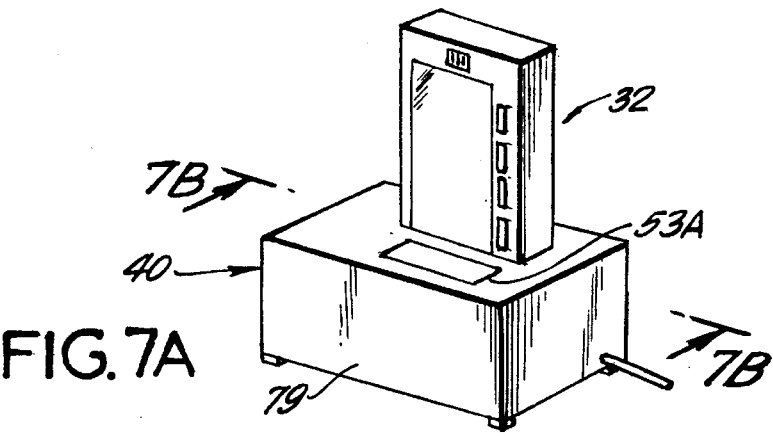
Figure 7B:
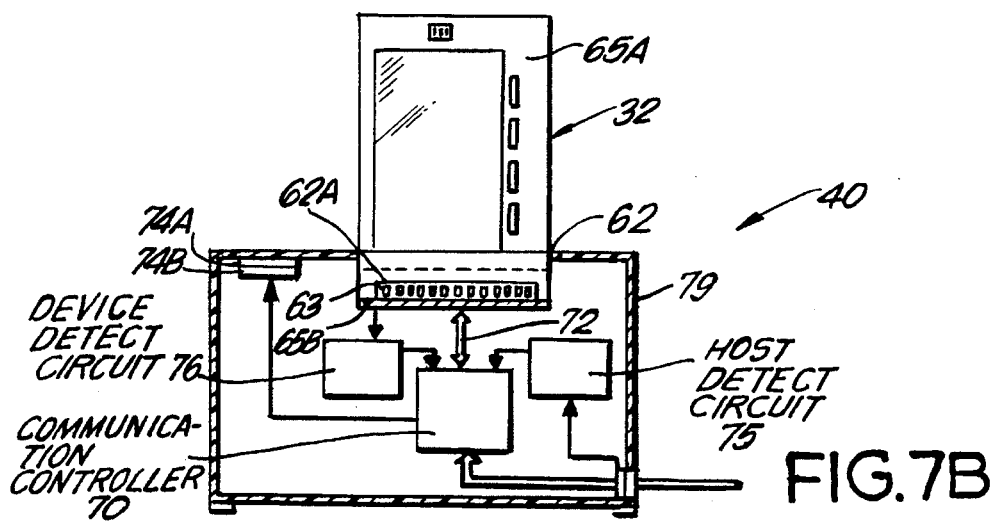
FIG. 7B is an elevated partially cross-sectional view taken along line 7B—7B of FIG. 7A, showing the computer-programmable medication alarm device being programmed with a graphical prescribed dosage schedule while inserted into the programming interface unit of the pharmacy computer system.

In the illustrative embodiment, data communication port 62 of medication alarm device 32 comprises a multi-pin connector 62A which is enclosed within a recess 63 formed in the side end wall 65B of the casing, as shown in FIGS. 7 and 7B. In the illustrative embodiment shown in FIG. 7B, multi-pin connector 62A includes a plurality of miniature conductor pins for transmitting and receiving data and timing and control signals utilized in, for example, a RS-232 or other serial-data protocol. Notably, the number of conductor pins required will be proportional to the word length of the data bytes that are transmitted from the programming interface unit to the medication alarm device.

As illustrated in FIGS. 6 and 6A, programming interface unit 40 comprises a number of components, namely: communication controller 70 having a program memory, e.g. ROM (not shown) for storage of a microcode-control program that governs the operation of the programming interface unit; buffer memory (e.g. RAM) 71 for buffering data packets received from the host processor; data communication ports 72 and 73 operably associated with communication controller 70; a visual display device 74 comprising 1×16 LCD character display 74A and an associated display interface circuitry 74B, for providing visual indications of the state of operation of the programming interface unit and the computer-programmable medication alarm device being programmed; and host and device detection circuitry 75 and 76 for detecting whether the pharmacy computer system and medication alarm device are physically interfaced. Preferably, electrical power for these components is provided from the pharmacy computer system via power lines passing through data communication port 39A.

As illustrated in FIGS. 5, 6, and 6A, data communication cable 77 is used to interconnect (i.e. interface) data communication ports 39A and 72. In this configuration, communication controller 70 is operably associated with host processor 33 and host detect circuit 75 provides a "Host-Detect" signal to communication controller 70. As illustrated in FIG. 7B, data communication port 73 comprises a multi-pin connector 73A matched to multi-pin connector 62A of the medication alarm device. As shown, multi-pin connector 73A is enclosed within a slot-like opening 78 (i.e. programming port) formed through the top wall of housing 79 containing the components of the programming interface unit. Preferably, multi-pin connector 73A includes a plurality of miniature conductor holes into which the pins of the multi-pin connector 62A are slidably received when the medication alarm device is plugged into slot-like opening 78 for programming with a prescribed dosage schedule. When medication alarm device 32 is plugged into programming port 78 and the connector pins are in electrical contact with the conductor contacts as shown in FIG. 7B, device detect circuit 76 provides a "Device-Detect" signal to communication controller 70. With both the "Host-Detect" and "Device-Detect" present at the communication controller, the "Programming-Ready" message is displayed on LCD character display 74A by signals generated by display interface/driver circuitry 74B. When interfaced in this manner to the communication controller of the programming interface unit, medication alarm device 32 is ready for programming.

Medication alarm device 32 has four primary modes of operation, namely: a dosage-schedule/standard-time programming mode illustrated in FIG. 7B; a standard-time display mode illustrated in FIG. 8A; a dosage schedule display mode illustrated in FIG. 8B; and a standard-time programming mode illustrated in FIG. 8C. Each of these modes of operation will be discussed below.

The dosage-schedule/standard-time programming mode automatically is entered by inserting a medication alarm device 32 into programming port 78 of the programming interface unit, as shown in FIGS. 7A and 7B. In this configuration, LCD display screen 66 is blank and "Programming-Ready" is displayed on LCD character display 74A. With a prescribed medication dosage schedule stored in data storage memory 35, the pharmacist enters a programming-function command to the host processor through a keyboard entry operation made on keyboard 36. Upon decoding the programming-function command, host processor 33 commences a dosage schedule programming protocol which involves the host processor transmitting a serial data stream to communication controller 70. Upon receiving and detecting a predetermined bit sequence in the transmitted data stream from the host processor, the communication controller causes the "Programming-Ready" message to disappear and the "Programming-Occurring" message to appear on LCD character display 74A. The transmitted data stream includes data packets representing the frames of graphical data comprising the prescribed dosage schedule. As this dosage schedule data is being received by the communication controller, it is buffered in RAM memory 71. In accordance with its control program, communication controller 70 transmits "Transit-Ready" packet to programmable timer/controller 51 and when the programmable timer/controller is ready to receive data packets, a "Receive-Ready" packet is transmitted from the programmable timer/controller to communication controller 70. In response, the communication controller begins transmitting dosage schedule data packets to programmable timer/controller 51. As these data packets are received, they are processed (e.g. data format conversion) and then frames of formatted dosage schedule data are stored at specified memory locations in data storage unit 50.

Upon completing the transmission of data relating to the prescribed dosage schedule, updated standard-time data is generated by a standard-time clock generator (not shown) in the pharmacy computer system and is transmitted to the communication controller of the programming interface unit. The communication controller then transmits this standard-time data to programmable timer/controller 51, which then stores this updated standard-time data in standard-time register 55. This data is then used immediately to update (i.e. synchronizing) the standard-time clock emulated by programmable timer/controller 51. After data packet reception has been completed and acknowledged by the programmable timer/controller, synchronization of the standard-time clock in the medication alarm device can be achieved by the programmable timer/controller (i) immediately accessing the updated standard-time data from the standard-time data register and (ii) using this data to adjust the standard-time being measured by the programmable timer/controller. When standard-time synchronization is completed, the communication controller causes the "Programming-Occurring" message to disappear and "Programming-Complete" message to appear on LCD character display 74A. At this stage of the process, the medication alarm device is programmed and ready for use.

Upon removing the medication alarm device from programming interface unit, the dosage-schedule/standard-time programming mode is exited and the standard-time display mode is automatically entered. In this mode, standard-time data 80 is displayed in the upper visual display field 81A, while patient, physician and information 26 are displayed in lower visual display field 81B, as shown in FIG. 8A. When it is desired to exit the standard-time display mode and enter the dosage schedule display mode for reviewing the programmed dosage schedule, key 55 indicated by "DS/DT DSPY." on the front panel is depressed. In the dosage schedule display mode, items of dosage schedule data are displayed in their respective visual display fields 82A, 82B, 82C and 82D as in a manner similar to that described above in connection with manually-programmable medication alarm device 1. The data contained in visual display fields 82A through 82D, represent a single frame of dosage schedule data particularly associated with a single dosage of medication to be administered in a particular amount, at a particular time and in a particular manner. When in this mode, each frame of dosage schedule data is indexed by a frame number (e.g. i=1, 2, 3, 4, . . . ) displayed in visual display field illustrated in FIG. 8B. By depressing key 56 indicated by "SEQ" in FIG. 8B, the programmed frames of dosage schedule data are sequenced from i=1, 2, 3 . . . N, where N can be any integer. In ophthalmic applications, N may be 1000 or even greater to provide up to one-thousand programmable administration times during a period of weeks or months or even a calendar year. In other embodiments however, the number of required dosage schedule frames suitable for a particular application, may be less than or greater than one-thousand.

In order to review the programmed dosage data for a particular frame (i.e. i=1, 2, . . . or N) in a prescribed dosage schedule, key 56 indicated by "SEQ" is depressed. Each time key 56 is depressed, data associated with the subsequent frame in the programmed dosage schedule is displayed. In order to return to the standard-time display mode, key 55 is depressed. The dosage schedule display mode can be reentered at any time by simply depressing key 55.

Each instance when the standard-time displayed equals an administration time in the programmed dosage schedule, programmable timer/controller 51 generates a control signal which is provided to alarm'signal generator 53. In response, an audible alarm signal is generated, preferably by a piezoelectric transducer, and alerts the patient to take his or her medication in accordance with the dosage schedule data being displayed in visual display fields 82A, 82B, 82C, and 82D of LCD device 53B, as illustrated in FIG. 8B. Preferably, the audible alarm signal is an intermittent "beep" tone which lasts for a predetermined time period (e.g. several minutes) before ceasing. To deactivate alarm signal generator 52 before it lapses on its own accord, the patient simply depresses key 57, indicated as "ALARM OFF" in FIG. 8A. Thereupon, programmable timer/controller 51 displays a " " mark in visual display field 82F, illustrated in FIG. 13B. As in medication alarm device 1, this mark is stored in memory 50 and is displayed at a later time in the dosage schedule display mode, to inform the patient (or pharmacist) that the prescribed dosage of medication has been taken in accordance with the programmed dosage schedule.

Figure 9A:
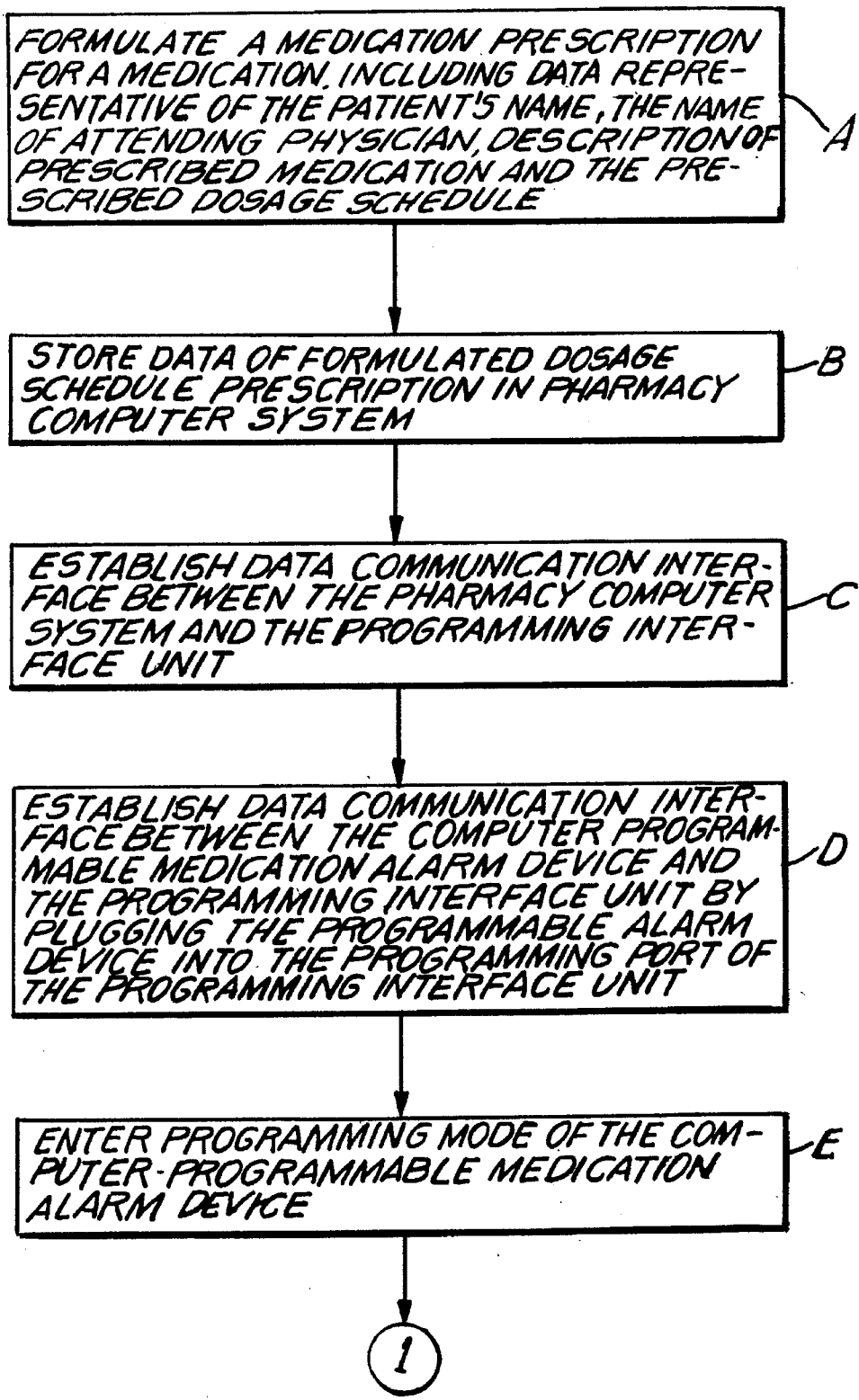
FIG. 9A and 9B taken together, shown a high level flow chart illustrating a method of programming the computer-programmable medication alarm device of the present invention using the pharmacy computer system illustrated in FIGS. 5 through 7B.
Figure 9B:
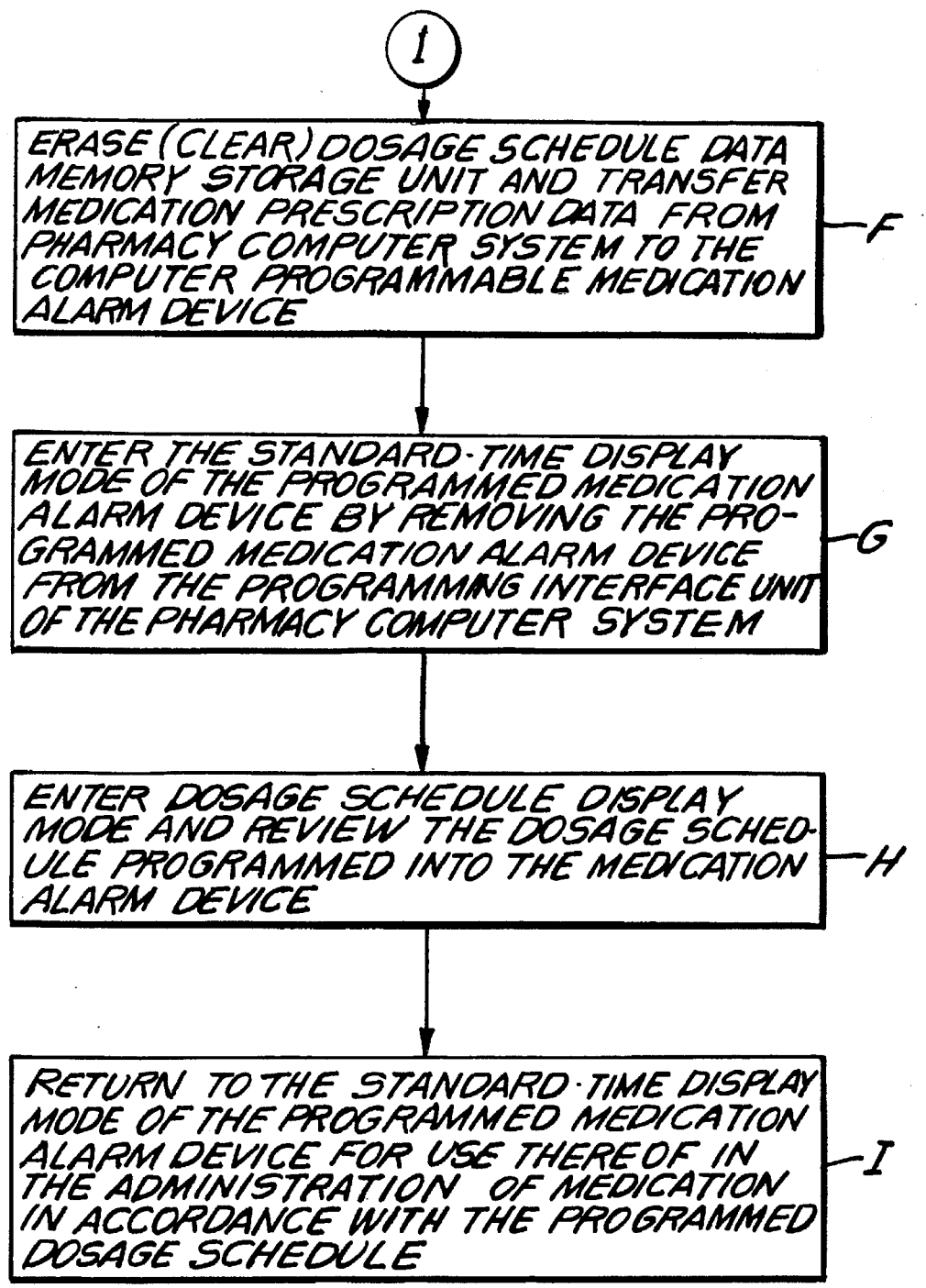

Referring to FIGS. 9A through 9B, in particular, a method of programming medication alarm device 32 using pharmacy computer system 31 and programming interface unit 40, will now be described.

As indicated at Block A in FIG. 9A, the first step of the method involves formulating a prescription for the medication being prescribed to the patient. As discussed in connection with FIG. 2 the medication schedule prescription will typically include graphical data representative of the patient's name (i.e. identification), the name of the attending physician, a description of the prescribed medication, and a specification of the prescribed medication dosage schedule.

Then, as indicated at Block B, the graphical data associated with the formulated medication prescription is stored in digital form in the pharmacy computer system Depending on how the dosage schedule prescription is formulated, the method of data storage may differ. For example, the medication prescription can be formulated on a personal computer system 45 at a doctor's office using a software program having dosage schedule programming logic and visual graphics capabilities. In this case, the formulated medication prescription can be digitized into a data stream, transmitted over a data communication link (e.g. PTSN) and received at pharmacy computer system 31. The received data of the medication prescription can then be stored in data storage memory 35, and therefrom a patient prescription file created and stored in the pharmacy computer system for subsequent use. Typically, the patient's prescription file will include information such as the patient's name, the name of the attending physician, a description of the prescribed medication, and the prescribed dosage schedule.

In an alternative embodiment, a doctor can call in the medication prescription to a pharmacist and from the prescription the pharmacist can create a patient prescription file. This approach will typically involve manually entering various items of prescription data into the pharmacy computer system. In the illustrative embodiment, this prescription data can be entered into data storage memory 35 of the pharmacy computer system by way of key entry operations performed using keyboard 36. To facilitate this tedious data entry procedure, a medication dosage schedule similar to that shown in FIGS. 2 and 2A, is preferably displayed on the display screen unit of the pharmacy computer system. Preferably, a computer software program having dosage schedule programming logic and visual graphics capabilities is used to simplify prescription data entry. The use of such a program will be particularly advantageous when prescribed dosage schedules are complicated in nature, as in the case of ophthalmic solutions and nasal and respiratory medications.

In many commercial environments where over-the-counter drugs are sold, prescribed dosage schedules for such medications can be pre-encoded by the manufacturer or pharmacy, using bar code symbols. The encoded bar code symbols can be compiled on one or more menu sheets accessible at the pharmacy counter where the pharmacy computer system will typically be installed. In such applications, bar code symbol reading device 37 can be linked to a data communication port of the pharmacy computer system (or into keyboard wedge interface device). Using the bar code symbol reading device, data associated with a particular dosage schedule can be rapidly entered into the pharmacy computer by simply reading a corresponding bar code symbol corresponding to the particular medication being purchased or prescribed.

After the prescribed dosage schedule and related prescription data have been entered into the pharmacy computer system, a data communication interface must be established between the pharmacy computer system and the programming interface unit in order to transfer this data to the medication alarm device. As indicated at Block C in FIG. 9A, this interface is achieved in the illustrative embodiment by ensuring that data communication cable 37 is properly connected between data communication port 40 of the pharmacy computer and data communication port 72 of the programming interface unit.

As indicated at Block D, a computer-programmable medication alarm device 32 is then plugged into the programming port of the programming interface device, as illustrated in FIGS. 7, 7A and 7B. When configured in the manner shown in FIG. 7B, a data communication interface will be established between the medication alarm device and the pharmacy computer system, and the "Programming-Ready" message display on LCD character display 74A.

To enter the programming mode of the medication alarm device as indicated at Block E in FIG. 9B, the pharmacist enters a programming-function command to the host processor by way of the pharmacy system keyboard. After completing "hand-shaking" protocols with the communication controller, the programmable timer/controller 51 clears (i.e. erases) data storage unit 50. Thereafter, the "Programming-Occurring" message is displayed on LCD character display 53B. As indicated at Block F, the host processor then proceeds to transfer from data storage memory 35 to the communication processor, those data packets comprising the formulated medication prescription. The received data packets are first buffered in buffer memory 71, then transmitted to programmable timer/controller 51 and subsequently stored in data storage unit 50. Upon completing the transmission of data relating to the prescribed dosage schedule, synchronization of the standard-time clock in the programmable medication alarm device is achieved by the programmable timer/controller in a manner described hereinabove. When standard-time synchronization is completed, the communication controller displays the message "Programming-Complete" on the LCD character display.

Upon removing the programmed medication alarm device from the programming interface unit, the standard-time display mode of the programmed device is automatically entered, as indicated in Block G of FIG. 9B. In this mode, two visual display fields are presented; the upper visual display field graphically displaying the standard-time, and the lower visual display field displaying patient, physician and medication information. At this stage of the method, the programmed medication alarm device can be attached to a mounting base which can be releasably attached to the container of the prescribed medication, as illustrated in FIG.

Figure 15:
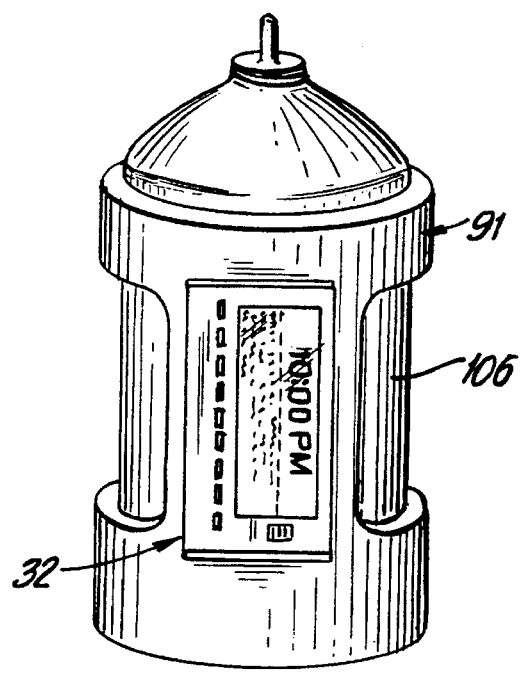
FIG. 15 is a perspective view of the medication container holder shown in FIG. 11, in which a conventional eye drop dispenser is slidably received for administration of eye drops in accordance with a medication dosage schedule programmed into the attached computer-programmable medication alarm device hereof.

10. Alternatively, the programmed medication device can be inserted into the recess of medication container holder 91 as illustrated in FIG. 15. The size of the medication container holder will, of course, be selected on the basis of outer diameter of the medication container used to contain the prescribed medication. Preferably, the pharmacist will have a range of such medication container holders of various dimensions from which to choose for use with the programmed medication alarm device.

As indicated at Block H of FIG. 9B, the pharmacist will typically want to review for accuracy, the programmed graphical information relating to the dosage schedule, the patient, the physician and the prescribed medication, that is, prior to giving the prescribed medication, its holder and the programmed medication alarm device to the patient. Programmed information relating to the standard-time, the patient's name, the physician's name and the description of the prescribed medication can be readily reviewed for accuracy by reading LCD screen. Programmed dosage schedule information can be displayed by depressing key 55, whereupon the dosage schedule display mode of the device is entered, illustrated in FIG. 8B. Then by sequentially depressing key 56, the pharmacist can review for accuracy, each frame of the programmed dosage schedule. If any errors are detected, the programmed medication alarm device can be reprogrammed and subsequently reviewed. As indicated at Block I, the dosage schedule display mode is exited and the standard-time display mode reentered by depressing key 55.

In some applications, it may be desired or required to provide a hard-copy medication prescription (e.g. dosage schedule) to the patient. In such instances, a hard copy dosage schedule 200 can be printed out on Printer 43 under the control of the host processor. Preferably, this hard-copy dosage schedule is printed on a paper strip which can be compactly folded into an ultra-thin packet having width and length dimensions equal to casing 65. In this way, they can be releasably secured to the back of casing 65 under attachment tabs (not shown), or between the back panel of casing 65 and the recess of medication container holder 90 to be described hereinafter. This hard-copy dosage schedule can be accessed by the patient in emergency situations where for example, the programmed medication alarm device is inadvertently damaged and rendered inoperative. Thereafter, medication container holder 90, 200 hard-copy dosage schedule, the prescribed medication, and the programmed medication alarm device can be assembled as illustrated in FIG. 15 and then given to the patient for administration in accordance with the programmed dosage schedule.

Having described the manually and computer programmable medication alarm devices of the present invention, apparatus for attaching these medication alarm devices to conventional medication containers will now be described below.

Figure 10:
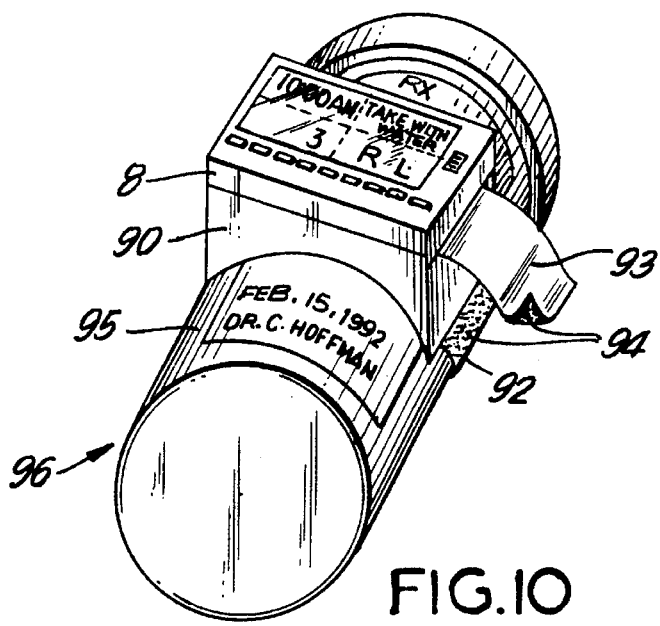
FIG. 10 is a perspective view of the manually-programmable medication alarm device shown attached to a mounting base which is releasably fastened to the side wall of a conventional medication container using a pair of fastening straps.

In the illustrative embodiment of FIG. 10, a pair of flexible straps 92 and 93, extending from the bottom portion of the side end walls of casing 23, permit the programmable medication alarm device hereof to be attached to virtually any support surface. As illustrated, a Velcro® type hook and loop fastener system 94 is provided to the surfaces of the flexible straps to permit releasable attachment of the casing to a support surface, which in FIG. 10, is the cylindrical wall surface 95 of a conventional medicine container 96. To facilitate mounting of the wafer-like casing 23 or 65 to medication container 96, a mounting support base 90 is attached to the back panel of the casing with straps 92 and 93 secured therebetween. As shown, the mounting support base of the illustrative embodiment has a semicircular surface which facilitates stable mounting against the cylindrical wall surface of conventional medicine containers. Preferably, the mounting support base is made of a lightweight material, such as elastic, rubber or foam.

Figures 11, 11A:
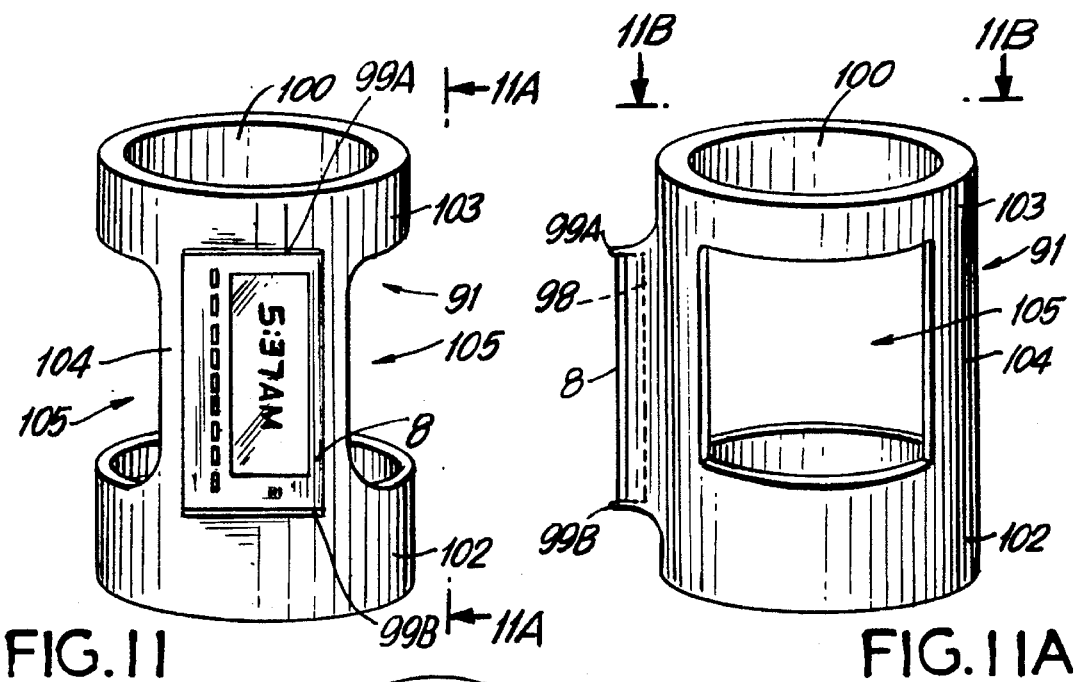
FIG. 11 is a perspective view of the manually-programmable medication alarm device shown installed within the side wall of a medication container holder adapted for receiving a variety of medication containers or dispensers, while permitting the dispensing of medication therefrom in a conventional manner.
FIG. 11A is a plan view of the medication container holder shown in FIG. 11 taken along line 11A—11A thereof.

As illustrated in FIGS. 11 through 14, the manually-programmable medication alarm device of the present invention is shown housed within a rectangular recess 98 formed in medication container holder 91. As shown, medication container holder is particularly adapted for receipt of a conventional eye-drop dispenser bottle, nasal-spray dispenser canister or other medication container. In the illustrative embodiment, medication alarm casing 8 is releasably held in recess 98 in a snap-fit manner by way of flanges 99A and 99B. By distorting holder 91 with the medication container removed therefrom, casing 8 can be inserted into recess 98, and retained in place by flanges 99A and 99B when the holder is relaxed in its non-distorted configuration, as shown in FIGS. 11 through 11B, in particular.

Figure 11B:
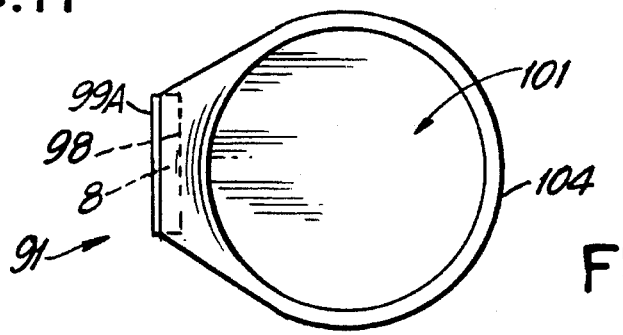
FIG. 11B is an elevated side view of the medication container holder shown FIGS. 11 and 11A, taken along line 11B—11B thereof.
Figure 12:
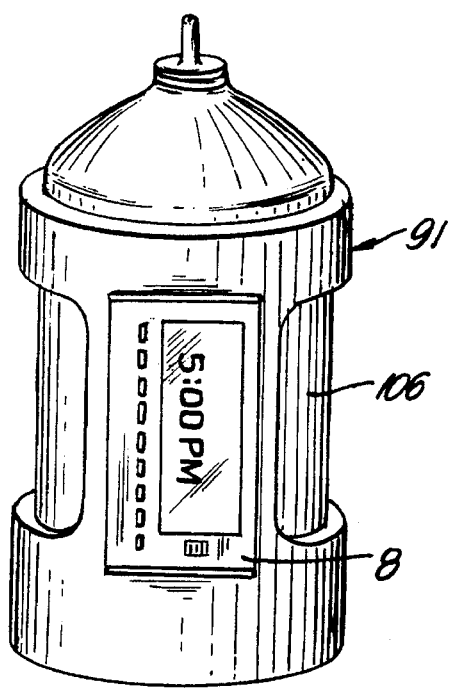
FIG. 12 is a perspective view of the medication container holder shown in FIG. 11, in which a conventional eye drop dispenser is slidably received for administration of eye drops in accordance with a graphical medication dosage schedule programmed into the attached manually-programmable medication alarm device.

As shown in FIG. 11, 11A and 11B, medication container holder 91 of the illustrative embodiment has a substantially cylindrical gross geometry, an opening 100 and an inner cavity 101. The inner cavity is adapted to slidably receive the body portion of a variety of medication dispensers or containers. As shown, medication container holder 91 also has a base portion 102, upper portion 103, and side wall portion 104 connecting portions 102 and 103. In addition, a pair of opposing side wall cut-out portions 105 are provided in side wall portion 104 so as to permit the patient to grasp holder 91 with, for example, an eye-drop bottle dispenser 106 slidably received therein, as shown in FIG. 12. Therewhile the patient can squeeze the flexible side wall of the eye-drop dispenser bottle in order to express a selected number of eye drops therefrom in accordance with the prescribed dosage schedule visually indicated on the LCD visual display. In the illustrative embodiment, the medication container holder is molded from a plastic material, although other suitable materials may be used.

Figure 13:
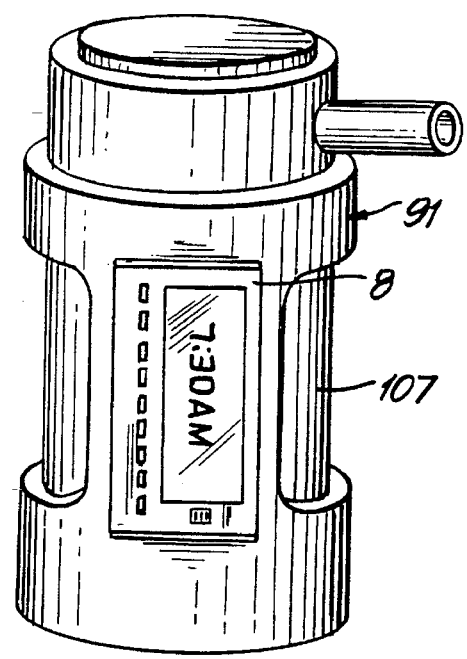
FIG. 13 is a perspective view of the medication container holder shown in FIG. 11, in which a conventional nasal spray dispenser is slidably received for administration of nasal spray in accordance with a graphical medication dosage schedule programmed into the attached manually-programmable medication alarm device.

In FIG. 13, medication container holder 91 of the present invention is shown being used with a conventional nasal spray dispenser 107. As illustrated, the body portion of nasal spray dispenser 107 is slidably received in the interior cavity of the holder without interfering with the overall functioning of the dispenser.

Figure 14:
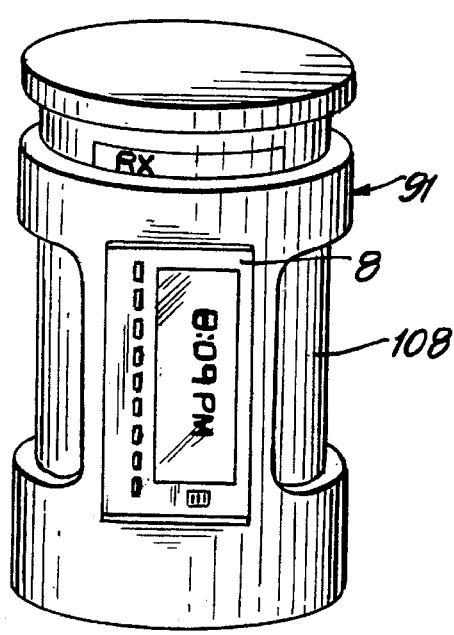
FIG. 14 is a perspective view of the medication container holder shown in FIG. 11, in which a conventional medication tablet container is slidably received for administration of medication tablets, pill or capsules in accordance with a graphical medication dosage schedule programmed into the attached manually-programmable medication alarm device.

In FIG. 14, the medication container holder of the present invention is shown being used with a conventional medication tablet container 108. As illustrated, the body portion of the tablet (i.e. pill) container is slidably received in the interior cavity of the receptacle without interfering with the overall functioning of the dispenser.

In alternative embodiments of the present invention, the side walls of the medication container holder of the present invention can be made of a flexible, pliant material, such as rubber or other functionally equivalent material. In this way, the medication container holder can be easily compressed between a patient's fingers for dispensing eye drops from a conventional eye drop bottle. Also, the side walls of the holder can be stretched as required to accommodate a range of medication containers each having different side wall diameters. In such embodiments, side wall recess portions 104 and 105 can be avoided, yet without sacrificing the functionality of the medication container holder.

Having described the best mode now contemplated for practising the present invention, it is within the principles of the present invention to use other techniques.

For example, the data communication interface between the data communication port of the computer programmable medication alarm device hereof and the programming interface unit can be achieved using opto-electronic coupling devices, obviating the need for an electrical-contact type interface as described hereinabove. In such an alternative embodiment, the programming port of the programming interface unit can include an infrared transmitter for generating an optically modulated data signal. The data communication input port of the computer-programmable medication alarm device would then include an infrared receiver for receiving the optically modulated data signal and demodulating the same to recover the transmitted data signal bearing the dosage schedule data.

In yet another alternative embodiment, the programming interface can be provided with a modem operably associated with the communication controller and a telecommunication switch. Between the telecommunication switch and the programming port, a dialing circuit can be provided. With a telecommunication line connected to the programming port, the dialing circuit can effectuate a telecommunication connection with a patient's telephone via a central switching station. The medication alarm device, on the other hand, can be provided with an acousto-electrical transducer and a modem operably associated with its data communication port and system bus. In this way, the programming interface unit can transmit digitally encoded data signals through the programming port, over the telecommunication line, across the central switching statnion(s) and to the patient's telephone hand-set. When brought in proximity with a hand-set, the audible data signals from the hand-set can be detected by the acousto-electrical transducer in the programmable medication alarm device. Such received data signals can then be demodulated using the modem, subsequently processed and stored in data storage unit 50, in a manner described hereinabove.

The computer-programmable medication alarm device of the present invention can be made so as to be programmable one or more times and thereafter disposed. Alternatively, the housing of the programmable medication alarm device hereof may be integrally formed with the medication container holder illustrated in FIGS. 11 through 11B.

In the computer-programmable medication alarm device of the present invention, graphical medication instructions of virtually any type can be prescribed by the doctor and processor-programmed into the medication alarm device for display in, for example, visual display field 82D. Also, while four distinct visual display fields have been shown in the illustrative embodiments, it is understood that these visual display fields may vary in form, number and dimensions without departing from the principles of the present invention.

In other embodiments, the programmable medication alarm devices hereof may be packaged in a casing which can be worn around the patient's wrist, or clipped to the patient's belt or shirt pocket. Alternatively, the housing may resemble a medallion which can be safely worn about the patient's neck.

While the particular embodiments shown and described above will be useful in many applications in the medication compliance art, further modifications of the present invention herein disclosed will occur to persons skilled in the art to which the present invention pertains. All such modifications are deemed to be within the scope and spirit of the present invention defined by the appended claims.

What is claimed is:

1. A portable medication alarm device for use in the administration of an eye medication prescribed to a patient which comprises:

a casing of physically thin dimensions;

data storage means, disposed in said casing, for storing data representative of at least one prescribed eye medication dosage schedule specifying a prescribed administration time, a prescribed dosage amount and a prescribed administration route for each eye medication dosage to be administered to said patient;

data programming means, disposed in said casing, for programming in said data storage means, data representative of said prescribed eye medication dosage schedule;

timing means, disposed in said casing, for timing the occurrence of each said prescribed administration time specified in said prescribed eye medication dosage schedule;

alarm signal generating means, disposed in said casing, for generating a dosage alarm signal in response to the timed occurrence of each said prescribed administration time;

display means, disposed in said casing, for visually displaying in response to the timed occurrence of each said administration time, a graphical representation of the prescribed dosage amount and the administration route for said medication dosage specified in said prescribed eye medication dosage schedule; and an eye medication dispenser bottle holder having a base portion, an upper portion with a substantially circular opening, a side wall portion connecting said base portion and said upper portion, an inner cavity accessible through said substantially circular opening, and adapted for slidable receipt of an eye medication dispenser bottle having flexible side walls and containing a quantity of said eye medication, said side wall portion permitting said patient to squeeze and deform the flexible side walls of said eye medication dispenser bottle so as to manually express from said eye medication dispenser bottle, a number of drops of eye medication in accordance with the prescribed dosage amount displayed on said display means, and to administer said drops into the eyes of said patient in accordance with the prescribed administration route visually displayed on said display means, and said casing being mounted to either said base portion, said upper portion or said side wall portion of said eye medication dispenser bottle holder.

2. The portable medication alarm of claim 1, wherein said dosage alarm signal is an audible signal and said display means comprises a visual display which displays said graphical representation of the prescribed dosage amount and the prescribed administration route for each said prescribed eye medication dosage.

3. The medication alarm device of claim 2, wherein said prescribed administration route is either the patient's left or right eye, and the said graphical representation corresponding to said patient's left and right eye comprises graphical characters L and R, respectively.

4. The portable medication alarm device of claim 1, wherein said data programming means comprises manual data entry means for manually programming in said data storage means by way of key entry operations, data representative of said prescribed eye medication dosage schedule.

5. The portable medication alarm device of claim 4, wherein said prescribed eye medication dosage schedule further comprises prescribed medication instructions, and wherein display means displays, in response to the timed occurrence of each said prescribed administration time, a graphical representation of the prescribed patient instructions specified in said prescribed eye medication dosage schedule.

6. The portable medication alarm device of claim 5, wherein said timing means further comprises means for measuring standard-time, and wherein said display means displays a graphical representation of said standard-time being measured.

7. The portable medication alarm device of claim 6, which further comprises (i) a dosage schedule programming mode for programming in said data storage means, data representative of said prescribed eye medication dosage schedule; (ii) a standard-time programming mode for programming standard-time data from which standard-time is to be measured; (iii) a standard-time display mode for displaying a graphical representation of the measured standard-time; (iv) a dosage schedule display mode for selectively displaying frames of graphical dosage schedule data programmed in said data storage means; and (v) a dosage alarm mode for displaying a frame of programmed graphical dosage schedule data in response to the timed occurrence of each said prescribed administration time.

8. The medication alarm device of claim 7, in which said display means has a plurality of visual display fields during operation in said dosage schedule display mode, for displaying a graphical representation of said prescribed administration time, dosage amount and administration route for each said prescribed eye medication dosage.

9. The portable medication alarm device of claim 1, which further comprises data receiving means disposed in said casing for receiving a data stream transmitted from a data supply means located exteriorly of said casing, and data programming means disposed in said casing, for automatically programming in said data storage means, at least a portion of the data contained in said received data stream, wherein said portion of said data is representative of said prescribed eye medication dosage.

10. The portable medication alarm device of claim 9, which further comprises a data communication port through said casing and which is interfaceable with a data communication port provided by said data supply means.

11. The portable medication alarm device of claim 10, wherein said prescribed eye medication dosage schedule further comprises prescribed eye medication instructions, and wherein said display means displays in response to the timed occurrence of each said prescribed administration time, the prescribed administration time and the prescribed eye medication instructions specific in said prescribed eye medication dosage schedule.

12. The portable medication alarm device of claim 1, wherein said side wall portion comprises at least one side wall cut-out portion for permitting said patient to squeeze and deform the flexible side walls of said eye medication dispenser bottle so as to manually express from said eye medication dispenser bottle, said number of drops of eye medication in accordance with the prescribed eye dosage amount displayed on said display means.

13. An eye medication dispenser bottle holder for use by a patient comprising:

a base portion;

an upper portion with a substantially circular opening;

a side wall portion connecting said base portion and said upper portion; and an inner cavity accessible through said substantially circular opening, and adapted for slidable receipt of an eye medication dispenser bottle having flexible side walls and containing a quantity of said eye medication;

said side wall portion permitting said patient to squeeze and deform the flexible side walls of said eye medication dispenser bottle so as to manually express from said eye medication dispenser bottle, a number of drops of eye medication into one or both eyes of said patient.

14. The eye medication dispenser bottle holder of claim 13, wherein said base portion, said upper portion and said side wall portion are made from a resilient plastic material.

15. The eye medication dispenser bottle holder of claim 13, wherein said side wall portion comprises at least one side wall cut-out portion for permitting said patient to squeeze and deform the flexible side walls of said eye medication dispenser bottle so as to manually express from said eye medication dispenser bottle, said number of drops of eye medication in accordance with the prescribed eye dosage amount displayed on said display means.

* * * * *